United States Patent [19]

Okabe et al.

[11] Patent Number: 5,082,943
[45] Date of Patent: Jan. 21, 1992

[54] NOVEL IMIDAZOLE DERIVATIVES

[75] Inventors: Susumu Okabe, Kyoto; Mitsuo Masaki; Tomio Yamakawa, both of Chiba; Hitoshi Matsukura, Saitama; Yutaka Nomura, Chiba, all of Japan

[73] Assignee: Nippon Chemiphar Co., Ltd., Tokyo, Japan

[21] Appl. No.: 658,424

[22] Filed: Feb. 20, 1991

Related U.S. Application Data

[63] Continuation of Ser. No. 392,364, Aug. 10, 1989, abandoned.

[30] Foreign Application Priority Data

Aug. 10, 1988 [JP] Japan .................. 63-199528
Nov. 24, 1988 [JP] Japan .................. 63-297856

[51] Int. Cl.$^5$ .................. C07D 401/12; C07D 215/38; C07D 233/66; C07D 403/12
[52] U.S. Cl. .................. 546/210; 546/171; 546/172; 546/173; 546/174; 546/177; 548/337; 548/336; 548/339; 548/323; 544/370; 540/603
[58] Field of Search ............... 546/210; 548/337, 339, 548/323

[56] References Cited

PUBLICATIONS

Okabe et al., Chem. Abstracts. vol. 108, No. 13; 133881w (1988).
Cox et al., Chem. Abstracts, vol. 109, No. 1; 6517q (1988).

Primary Examiner—Johann Richter
Attorney, Agent, or Firm—McAulay Fisher Nissen Goldberg & Kiel

[57] ABSTRACT

Disclosed are novel imidazole derivatives having the formula:

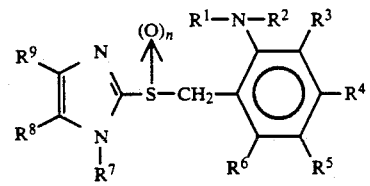

wherein $R^1$ and $R^2$ are H, alkyl, cycloalkyl, aryl, aralkyl or halogen-substituted alkyl, or $R^1$ and $R^2$ are combined to form a heterocyclic ring; $R^3$, $R^4$, $R^5$ and $R^6$ are H, halogen, alkoxy, aralkyloxy, alkyl, alkoxycarbonyl, nitro, amino, acyl, fluorine substituted-alkyl, or fluorine substituted-alkoxy, or $R^3$ is combined with $R^2$ to form a heterocyclic ring; $R^8$ and $R^9$ are H, halogen, alkoxy, alkyl, alkoxycarbonyl, nitro, amino, acyl, fluorine substituted-alkyl, fluorine substituted-alkoxy, or aryl group which may have a substituent, or $R^8$ and $R^9$ are combined to form an alicyclic ring; $R^7$ is, where $R^8$ and $R^9$ are not combined, H, and, where $R^8$ and $R^9$ are combined, H, alkyl which may have a substituent, aryl which may have a substituent, arylcarbonyl which may have a substituent, or a sulfur-containing heterocyclic group; and n is 0 or 1. The new imidazole derivatives are effective particularly as anti-ulcer agents.

12 Claims, No Drawings

NOVEL IMIDAZOLE DERIVATIVES

BACKGROUND OF THE INVENTION

1. Field of Invention

The present invention relates to a novel imidazole derivative and an anti-ulcer agent containing the imidazole derivative as an active ingredient.

2. Description of Prior Art

GB 2163747 describes that benzimidazole derivatives having the formula (A):

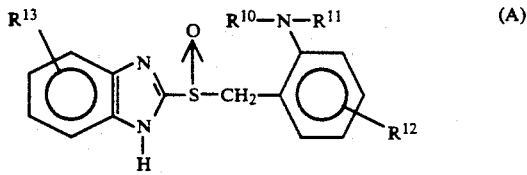

wherein each of $R^{10}$ and $R^{11}$ is hydrogen or a lower alkyl group, and at least one of $R^{12}$ and $R^{13}$ is a halogen atom, trifluoromethyl, a lower alkyl group, a lower alkoxy group, a lower alkoxycarbonyl group or amino, are effective as anti-ulcer agents showing $H^+ + K^+$ ATPase inhibitory action.

EP 234690A describes that imidazole derivatives having an aromatic pyridine ring fused with the imidazole ring which are represented by the formula (B):

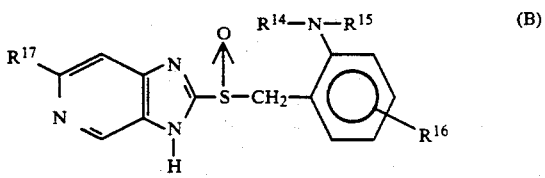

wherein each of $R^{14}$ and $R^{15}$ is hydrogen or a lower alkyl group and each of $R^{16}$ and $R^{17}$ is hydrogen, a lower alkoxy group or a lower alkyl group, are effective as anti-ulcer agents showing $H^+ + K^+$ ATPase inhibitory action.

SUMMARY OF THE INVENTION

An object of the present invention is to provide a new imidazole derivative showing a high anti-ulcer action as well as improved safety.

It has been discovered by the present inventor that imidazole derivative having no aromatic ring fused with the imidazole ring which is represented by the formula (I):

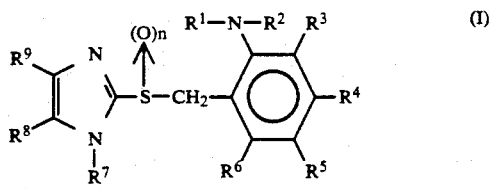

wherein:

each of $R^1$ and $R^2$ independently is hydrogen, a lower alkyl group having 1-8 carbon atoms, a cycloalkyl group having -8 carbon atoms, an aryl group, an aralkyl group having 1-4 carbon atoms in its alkyl chain, or a halogen atom substituted-alkyl group having 1-8 carbon atoms, or $R^1$ and $R^2$ are combined to form, together with nitrogen atom to which $R^1$ and $R^2$ are attached, one of 5-8 membered heterocyclic rings;

each of $R^3$, $R^4$, $R^5$ and $R^6$ independently is hydrogen, a halogen atom, a lower alkoxy group having 1-6 carbon atoms, an aralkyloxy group having 1-4 carbon atoms in its alkyl chain, a lower alkyl group having 1-6 carbon atoms, an alkoxycarbonyl group having 2-7 carbon atoms, nitro, amino, a lower acyl having 1-6 carbon atoms, a fluorine substituted-lower alkyl group having 1-6 carbon atoms, or a fluorine substituted-lower alkoxy group having 1-6 carbon atoms, or $R^3$ is combined with $R^2$ to form, together with nitrogen atom to which $R^2$ is attached and two carbon atoms of benzene ring to which $R^3$ is attached, one of 5-8 membered heterocyclic rings;

each of $R^8$ and $R^9$ independently is hydrogen, a halogen atom, a lower alkoxy group having 1-6 carbon atoms, a lower alkyl group having 1-6 carbon atoms, an alkoxycarbonyl group having 2-7 carbon atoms, nitro, amino, a lower acyl having 1-6 carbon atoms, a fluorine substituted-lower alkyl group having 1-6 carbon atoms, a fluorine substituted-lower alkoxy group having 1-6 carbon atoms, or an aryl group which may have at least one substitutent selected from the group consisting of a lower alkyl group having 1-6 carbon atoms, a lower alkoxy group having 1-6 carbon atoms and a halogen atom, or $R^8$ and $R^9$ are combined to form, together with two carbon SO atoms of imidazole ring to which $R^8$ and $R^9$ is attached, one of 5-8 membered alicyclic rings;

$R^7$ is hydrogen, where $R^8$ and $R^9$ are not combined. In the case that $R^8$ and $R^9$ are combined to form the alicyclic ring, $R^7$ is hydrogen, a lower alkyl group having 1-6 carbon atoms which may have at least one substituent selected from the group consisting of an aryl group, hydroxyl, a lower alkoxy group having 1-6 carbon atoms, and a halogen atom, an aryl group which may have at least one substituent selected from the group consisting of a lower alkyl group having 1-6 carbon atoms, a lower alkoxy group having 1-6 carbon atoms, and a halogen atom, an arylcarbonyl group which may have at least one substituent selected from the group consisting of a lower alkyl group having 1-6 carbon atoms, a lower alkoxy group having 1-6 carbon atoms, and a halogen atom, or a -8 membered heterocyclic group containing a sulfur atom as its ring member; and n is 0 or 1, has an excellent gastric juice inhibitory action.

DETAILED DESCRIPTION OF THE INVENTION

The imidazole derivative of the formula (I) can be represented by either a thio-type compound of the following formula (II) or a sulfinyl-type compound of the following formula (III):

Thio-type compound

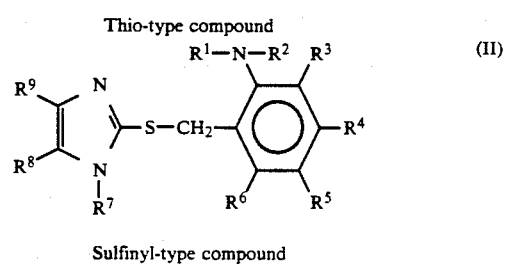

Sulfinyl-type compound

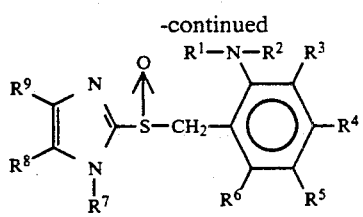

In the formulae (II) and (III), $R^1$, $R^2$, $R^3$, $R^4$, $R^5$, $R^6$, $R^7$, $R^8$, and $R^9$ have the same meanings as defined for the formula (I).

In the formulae (I), (II) and (III) of the imidazole derivative of the present invention. $R^1$, $R^2$, $R^3$, $R^4$, $R^5$, $R^6$, $R^7$, $R^8$, $R^9$ and "n" have the following meanings.

$R^1$ and $R^2$ are the same or different from each other and each represents is hydrogen; an alkyl group having 1-8 carbon atoms such as methyl, ethyl, propyl, n-butyl, isobutyl, tert-butyl, pentyl, hexyl, heptyl, octyl or 2-ethylhexyl; a cycloalkyl group having 5-8 carbon atoms such as cyclopentyl, cyclohexyl. cycloheptyl, or cyclooctyl; an aryl group such as phenyl or naphthyl: an aralkyl group which has 1-4 carbon atoms in its alkyl chain and may have one or more substituents (e.g., alkyl having 1-6 carbon atoms, alkoxy having 1-6 carbon atoms, or halogent), such as benzyl. phenylethyl, phenylpropyl, naphthylmethyl, monomethylbenzyl, dimethylbenzyl mono ethylbenzyl, diethylbenzyl, trimethylbenzyl, methylethylbenzyl, monomethoxybenzyl, dimethoxybenzyl, trimethoxybenzyl. monoethoxybenzyl, diethoxybenzyl, methoxyethoxybenzyl, chlorobenzyl, bromobenzyl, chlorophenylethyl, bromophenylethyl, chloromethylbenzyl, or bromomethoxybenzyl; or an halogen atom-substituted alkyl group having 1-8 carbon atoms such as fluoromethyl, difluoromethyl. trifluoromethyl, chloromethyl, fluoroethyl or trifluoroethyl. Otherwise, $R^1$ and $R^2$ are combined to form, together with nitrogen atom to which $R^1$ and $R^2$ are attached, one of 5-8 membered heterocyclic rings such as pyrrolidine, piperidine or perhydroazepine.

$R^3$, $R^4$, $R^5$ and $R^6$ are, all or in part, the same or different from each other, and each represents hydrogen; a halogen atom such as fluorine, chlorine, bromine or iodine; an alkoxy group having 1-6 carbon atoms such as methoxy, ethoxy, propoxy, isopropoxy, butoxy, isobutoxy. tert-butoxy, pentoxy or hexyloxy; an aralkyloxy group having 1-4 carbon atoms in its alkyl chain such as benzyloxy, phenylethoxy, phenylpropoxy, or naphthylmethoxy; an alkyl group having 1-6 carbon atoms such as methyl, ethyl, propyl, isopropyl, n-butyl, isobutyl, tert-butyl, pentyl, neopentyl, or hexyl; an alkoxycarbonyl group having 2-7 carbon atoms such as methoxycarbonyl, ethoxycarbonyl, propoxycarbonyl, isopropoxycarbonyl, butoxycarbonyl, pentoxycarbonyl or hexyloxycarbonyl; nitro; amino; an acyl having 1-6 carbon atoms such as formyl, acetyl, propionyl, isopropionyl, butyryl, isobutyryl, valeryl or isovaleryl; a fluorine substituted-alkyl group having 1-6 carbon atoms such as fluoromethyl, difluoromethyl, trifluoromethyl, fluoroethyl, trifluoroethyl, fluoropropyl, fluorobutyl, fluoropentyl, or fluorohexyl; or a fluorine substituted-alkoxy group having 1-6 carbon atoms such as flouromethoxy, difluoromethoxy, trifluoromethoxy, fluoroethoxy, fluoropropoxy, fluoroisopropoxy, fluorobutoxy. fluoropentoxy, fluorohexyloxy. Otherwise, $R^3$ is combined with $R^2$ to form a divalent alkylene ring such as ethylene, propylene (i.e., trimethylene), tetramethylene which may have one or more substituents such as alkyl having 1-4 carbon atoms such as methyl, ethyl, propyl, isopropyl, alkoxy having 1-4 carbon atoms such as methoxy or ethoxy, or halogen such as chlorine or bromine.

$R^8$ and $R^9$ are the same or different from each other, and represents hydrogen; a halogen atom such as fluorine, chlorine, bromine or iodine; an alkoxy group having 1-6 carbon atoms such as methoxy, ethoxy, propoxy, butoxy, isobutoxy, tert-butoxy, pentoxy, or hexyloxy; an alkyl group having 1-6 carbon atoms such as methyl, ethyl, propyl, isopropyl, butyl, isobutyl, tert-butyl, pentyl or hexyl; an alkoxycarbonyl group having 2-7 carbon atoms methoxycarbonyl, ethoxycarbonyl, propoxycarbonyl, butoxycarbonyl, isobutoxycarbonyl, pentoxycarbonyl, or hexyloxycarbonyl; nitro; amino; an acyl having 1-6 carbon atoms such as formyl, acetyl, propionyl, butyryl, isobutyryl, tert-butyryl, valeryl or isovaleryl; a fluorine substituted-alkyl group having 1-6 carbon atoms such as fluoromethyl, difluoromethyl, trifluoromethyl, fluoroethyl, trifluoroethyl, fluoropropyl, fluorobutyl, fluoropentyl or fluorohexyl; or a fluorine substituted-alkoxy group having 1-6 carbon atoms such as flouromethoxy, difluoromethoxy, trifluoromethoxy, fluoroethoxy, fluoropropoxy, fluorobutoxy, fluoropentoxy or fluorohexyloxy; or an aryl group (e.g., phenyl and naphthyl) which may have at least one substituent (generally one, two or three substituents) selected from the group consisting of an alkyl group having 1-6 carbon atoms (e.g., methyl, ethyl, propyl, isopropyl, butyl, isobutyl and tert-butyl), an alkoxy group having 1-6 carbon atoms (e.g., methoxy, ethoxy, propoxy, isopropoxy, butoxy, isobutoxy and tert-butoxy) and a halogen atom (e.g., fluorine, chlorine, bromine, and iodine). Otherwise, $R^8$ and $R^9$ are SO combined to form, together with two carbon atoms of imidazole ring to which $R^8$ and $R^9$ is attached, one of -8 membered alicyclic rings such as cyclopentenyl, cyclohexenyl, methylcyclohexenyl, dimethylcyclohexenyl or cycloheptyl.

$R^7$ represents hydrogen in the case that $R^8$ and $R^9$ are not combined together. In the case that $R^8$ and $R^6$ are combined to form the alicyclic ring, $R^7$ represents hydrogen; an alkyl group having 1-6 carbon atoms (e.g., methyl, ethyl, propyl, isopropyl, butyl, isobutyl, tert-butyl, pentyl and hexyl) which may have at least one substituent (generally one, two or three substituents) selected from the group consisting of an aryl group (e.g., phenyl and naphthyl), hydroxyl, an alkoxy group having 1-6 carbon atoms (e.g., methoxy, ethoxy, propoxy, isopropoxy, butoxy, isobutoxy, tert-butoxy, pentoxy and hexyloxy) and a halogen atom (e.g., fluorine, chlorine, bromine and iodine); an aryl group (e.g., phenyl and naphthyl) which may have at least one substituent (generally one, two or three substituents) selected from the group consisting of an alkyl group having 1-6 carbon atoms (methyl, ethyl, propyl, isopropyl, butyl, isobutyl. tert-butyl, pentyl and hexyl), an alkoxy group having 1-6 carbon atoms (e.g., methoxy, ethoxy, propoxy, isopropoxy, butoxy, isobutoxy, tert-butoxy, pentoxy and hexyloxy). and a halogen atom (e.g., fluorine, chlorine, bromine and iodine); an arylcarbonyl group which may have at least one substituent (generally one, two or three substituents) selected from the group consisting of an alkyl group having 1-6 carbon atoms (e.g., methyl, ethyl, propyl, isopropyl, butyl, isobutyl, tert-butyl, pentyl and hexyl), an alkoxy group having 1-6 carbon atoms (e.g., methoxy, ethoxy, propoxy, isopropoxy, butoxy, isobutoxy, tert-butoxy, pentoxy and hexyloxy). and a halogen atom (e.g., fluorine, chlorine, bromine and iodine); or a -8 SO membered heterocyclic group containing a sulfur atom such as thiophenyl, and thiazolyl.

"n" for number of oxygen atom is 0 or 1.

An imidazole derivative of the formula (I) wherein "n" is 0 (namely, thio-type compound of the formula (II)) S5 can be prepared by reaction of an aminobenzene derivative of the following formula (IV) with an imidazole derivative (V):

Aminobenzene derivative

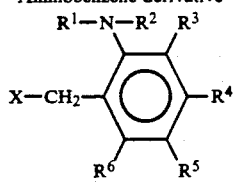 (IV)

Imidazole derivative

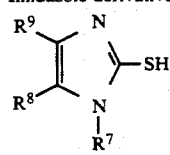 (V)

In the formulae (IV) and (V), $R^1$, $R^2$, $R^3$, $R^4$, $R^5$, $R^6$, $R^7$, $R^8$, and $R^9$ have the same meanings as defined for the formula (I), and X is a releasable group such as a halogen atom (e.g, chlorine or bromine), tosyloxy or mesyloxy.

The above reaction between a compound of the formula (IV) and a compound of the formula (V) can be performed at a temperature from room temperature to the reflux temperature for a period of 30 min. to 24 hrs., in an inert solvent such as benzene, ethanol or acetone. The reaction can be carried out in the presence of an alkali agent such as NaOH, KOH, $K_2CO_3$, or $NaHCO_3$, for trapping an acid produced in the reaction.

An imidazole derivative of the formula (I) wherein "n" is 1 (namely, sulfinyl-type derivative of the formula (III)) can be prepared by oxydizing the above-obtained thio-type compound of the formula (II).

The procedure of the oxidation reaction of the thio-type compound of the formula (II) to prepare the sulfinyl-type derivative can be performed in the conventional manner. For instance, a compound of the formula (II) can be oxidized using an oxidizing agent such as aqueous hydrogen peroxide in the presence of a metal ion (e.g., vanadium, molybdenum, or tungsten), an organic peroxide (e.g., m-chloroperbenzoic acid or tert-butylhydroperoxide), or sodium hypochlorite. The reaction can be performed in an inert solvent such as chloroform. dichloromethane, methanol, or ethyl acetate at a temperature in the range of $-30°$ C. to $50°$ C., preferably $-15°$ C. to $5°$ C.

Representative examples of the imidazole derivatives represented by the formulae (I), (II) and (III) are those which have $R^1$, $R^2$, $R^3$, $R^4$, $R^5$, $R^6$, $R^7$, $R^8$ and $R^9$ as defined in Table 1.

TABLE 1

| No. | $R^1$ | $R^2$ | $R^3$ | $R^4$ | $R^5$ | $R^6$ | $R^7$ | $R^8$ | $R^9$ |
|---|---|---|---|---|---|---|---|---|---|
| 1 | H | H | H | H | H | H | H | H | H |
| 2 | H | Me | H | H | H | H | H | H | H |
| 3 | Me | Me | H | H | H | H | H | H | H |
| 4 | H | Me | H | H | H | H | H | Cl | H |
| 5 | H | Me | H | H | H | H | H | Bu | H |
| 6 | H | Me | H | H | H | H | H | $CO_2Et$ | H |
| 7 | H | Me | H | H | H | H | H | Ph | H |
| 8 | H | Me | H | H | H | H | H | $NO_2$ | H |
| 9 | H | Me | Me | H | H | H | H | H | H |
| 10 | H | Me | H | H | Me | H | H | H | H |
| 11 | H | Me | H | H | H | Me | H | H | H |
| 12 | H | Me | H | Me | H | Me | H | H | H |
| 13 | H | Me | H | Me | OMe | Me | H | H | H |
| 14 | H | Me | H | H | OMe | H | H | H | H |
| 15 | H | Me | H | OMe | OMe | H | H | H | H |
| 16 | H | Me | H | H | OMe | OMe | H | H | H |
| 17 | H | Me | H | H | $OCF_3$ | H | H | H | H |
| 18 | H | Me | H | $NO_2$ | H | H | H | H | H |
| 19 | H | Me | H | Cl | H | H | H | H | H |
| 20 | H | Me | H | H | H | H | H | Me | H |
| 21 | H | Me | H | H | Me | H | H | Me | H |
| 22 | H | Me | H | H | OMe | H | H | Me | H |
| 23 | H | Et | H | H | H | H | H | Me | H |
| 24 | H | Et | H | H | Me | H | H | Me | H |
| 25 | H | Et | H | H | OMe | H | H | Me | H |
| 26 | H | i-Bu | H | H | H | H | H | Me | H |
| 27 | H | Me | H | H | H | H | H | Et | H |
| 28 | H | Me | H | H | H | H | H | $CF_3$ | H |
| 29 | H | Me | H | H | H | H | H | $CH_2CF_3$ | H |
| 30 | H | Me | H | H | OEt | H | H | H | H |
| 31 | H | Me | H | H | OBzl | H | H | H | H |
| 32 | H | Et | H | H | H | H | H | H | H |
| 33 | H | Et | H | H | Me | H | H | H | H |
| 34 | H | Et | H | H | OMe | H | H | H | H |
| 35 | H | Pr | H | H | H | H | H | H | H |
| 36 | H | i-Pr | H | H | H | H | H | H | H |
| 37 | H | i-Bu | H | H | H | H | H | H | H |
| 38 | H | i-Bu | H | H | Me | H | H | H | H |
| 39 | H | I-Bu | H | H | OMe | H | H | H | H |
| 40 | H | NeoPentyl | H | H | H | H | H | H | H |
| 41 | H | Hex | H | H | H | H | H | H | H |

TABLE 1-continued

| No. | R¹ | R² | R³ | R⁴ | R⁵ | R⁶ | R⁷ | R⁸ | R⁹ |
|---|---|---|---|---|---|---|---|---|---|
| 42 | H | c-Pent | H | H | H | H | H | H | H |
| 43 | H | c-Hex | H | H | H | H | H | H | H |
| 44 | H | CH₂CF₃ | H | H | H | H | H | H | H |
| 45 | H | Ph | H | H | H | H | H | H | H |
| 46 | H | Bzl | H | H | H | H | H | H | H |
| 47 | H | Et | H | H | OMe | Me | H | H | H |
| 48 | H | i-Bu | H | H | OMe | Me | H | H | H |
| 49 | —(CH₂)₄— | | H | H | H | H | H | H | H |
| 50 | H | —(CH₂)₃— | | H | H | H | H | H | H |
| 51 | H | Me | H | H | H | H | H | Me | Me |
| 52 | H | H | H | H | H | H | H | Et | Et |
| 53 | H | Me | H | H | H | H | H | Et | Et |
| 54 | H | Me | H | H | H | H | H | Me | Et |
| 55 | Me | Me | H | H | H | H | H | Et | Et |
| 56 | H | Me | H | H | H | H | H | Pr | Et |
| 57 | H | Me | H | H | H | H | H | Ph | Ph |
| 58 | H | i-Bu | H | H | H | H | H | Et | Et |
| 59 | H | H | H | H | Me | H | H | Et | Et |
| 60 | H | Et | H | H | H | H | H | Et | Et |
| 61 | H | H | H | H | H | H | H | —(CH₂)₄— | |
| 62 | H | Me | H | H | H | H | H | —(CH₂)₄— | |
| 63 | Me | Me | H | H | H | H | H | —(CH₂)₄— | |
| 64 | H | Et | H | H | H | H | H | —(CH₂)₄— | |
| 65 | H | i-Bu | H | H | H | H | H | —(CH₂)₄— | |
| 66 | H | Hex | H | H | H | H | H | —(CH₂)₄— | |
| 67 | H | H | H | H | Me | H | H | —(CH₂)₄— | |
| 68 | H | Me | H | H | Me | H | H | —(CH₂)₄— | |
| 69 | H | Me | H | H | H | Me | H | —(CH₂)₄— | |
| 70 | H | Me | H | Me | H | Me | H | —(CH₂)₄— | |
| 71 | H | Me | H | H | OMe | H | H | —(CH₂)₄— | |
| 72 | H | Me | H | H | OBzl | H | H | —(CH₂)₄— | |
| 73 | H | Me | H | Me | OMe | Me | H | —(CH₂)₄— | |
| 74 | H | Me | H | H | OCF₃ | H | H | —(CH₂)₄— | |
| 75 | H | Me | H | Cl | H | H | H | —(CH₂)₄— | |
| 76 | H | —(CH₂)₃— | | H | H | H | H | —(CH₂)₄— | |
| 77 | H | c-Hex | H | H | H | H | H | —(CH₂)₄— | |
| 78 | H | c-Pent | H | H | H | H | H | —(CH₂)₄— | |
| 79 | —(CH₂)₅— | | H | H | H | H | H | —(CH₂)₄— | |
| 80 | H | Me | H | H | H | H | H | —CH₂C(CH₂)₂—<br>\|<br>(Me)₂ | |
| 81 | H | Me | H | H | H | H | H | —(CH₂)₃C—<br>\|<br>(Me)₂ | |
| 82 | H | Me | H | H | H | H | H | —(CH₂)₃— | |
| 83 | H | Me | H | H | H | H | H | —(CH₂)₅— | |
| 84 | H | i-Bu | H | H | OMe | OMe | H | H | H |
| 85 | H | i-Bu | H | H | OCF₃ | H | H | H | H |
| 86 | H | i-Bu | H | H | Cl | H | H | H | H |
| 87 | H | i-Bu | H | H | NO₂ | H | H | H | H |
| 88 | H | i-Bu | H | H | H | OMe | H | H | H |
| 89 | H | i-Bu | H | H | F | H | H | H | H |
| 90 | H | i-Bu | H | H | H | Me | H | H | H |
| 91 | H | i-Bu | H | Cl | H | H | H | H | H |
| 92 | H | i-Bu | H | Me | H | H | H | H | H |
| 93 | H | i-Bu | H | H | H | Cl | H | H | H |
| 94 | H | i-Bu | Me | H | H | H | H | H | H |
| 95 | H | i-Bu | OMe | H | H | H | H | H | H |
| 96 | H | Bu | H | H | H | H | H | H | H |
| 97 | H | CH₂—<br>—Ph(4-OMe) | H | H | H | H | H | H | H |
| 98 | H | CH₂—<br>—Ph(3,4,5-(OMe)₃) | H | H | H | H | H | H | H |
| 99 | H | CH₂—<br>—Ph(2,4-Me₂) | H | H | H | H | H | H | H |
| 100 | H | CH₂CH₂—<br>—Ph(4-Cl) | H | H | OMe | H | H | H | H |
| 101 | H | Me | H | H | CO₂Me | H | H | H | H |
| 102 | H | Me | H | NH₂ | H | H | H | H | H |
| 103 | H | H | H | H | Ac | H | H | H | H |
| 104 | H | Me | H | i-Bu | H | H | H | H | H |
| 105 | H | Me | H | H | Oi-Pr | H | H | H | H |
| 106 | H | Me | H | H | i-Bu | H | H | H | H |
| 107 | H | t-Bu | H | H | H | H | H | H | H |

TABLE 1-continued

| No. | R$^1$ | R$^2$ | R$^3$ | R$^4$ | R$^5$ | R$^6$ | R$^7$ | R$^8$ | R$^9$ |
|---|---|---|---|---|---|---|---|---|---|
| 108 | H | i-Pen | H | H | H | H | H | H | H |

Remarks:
H: hydrogen.
Me: methyl,
Et: ethyl,
Pr: propyl,
i-Pr: isopropyl,
Bu: butyl,
i-Bu: isobutyl,
t-Bu: tert-butyl,
i-Pen: isopentyl,
Hex: hexyl,
c-Hex: cyclohexyl,
c-Pent: cyclopentyl,
Ph: phenyl,
Bzl: benzyl,
OMe: methoxy,
Oi-Pr: isopropoxy,
OCF$_3$: trifluoromethoxy,
Ac: acetyl,
CO$_2$Et: ethylcarbonyl,
OBzl: benzyloxy The pharmacological effects were tested with respect to some representative compounds of the formula (I) of the invention. The test results are given below.

(1) H$^+$ + K$^+$ ATPase Inhibitory Effects (a) Rabit gastric mucosa

Following the method of Forte et al (J. Applied Physiol., 32, 714–717 (1972)), gastric acid secretory cells of a rabbit gastric mucosa were isolated. A vesicle containing H$^+$ + K$^+$ ATPase was prepared by centrifuging the cells in Ficoll of discontinuous density gradient. After the enzyme was incubated at room temperature for 25 min. in 0.5 ml of a solution which contained 5 mM of an imidazole buffer (pH 6.0) and $2 \times 10^{-4}$M of each test compound, the mixture was heated to 37° C. The mixture was then allowed to stand for further 5 min. To the mixture was added 0.5 ml of a solution which contained 4 mM of magnesium chloride, 80 mM of an imidazole buffer (pH 7.4), 20 mM of potassium chloride and 4 mM of ATP. The resulting mixture was reacted at 37° C. for 15 min. and 1 ml of a 24% trichloroacetic acid was then added to terminate the reaction. The inorganic phosphorus liberated was quantitatively determined by the method proposed by Taussky and Shorr (J. Biol. Chem., 202, 075–685 (1953)). The ATPase activity was determined from the obtained inorganic phosphorus value.

The above procedure was repeated except for not using potassium chloride to determine an ATPase activity in the absence of potassium chloride.

The desired K$^+$-dependent ATPase activity was calculated by subtracting the ATPase activity value determined in the absence of KCl from the ATPase activity value determined in the presence of KCl.

The results are set forth in Table 2.

TABLE 2

| Tested Compound (Example No.) | H$^+$ + K$^+$ ATPase inhibitory action (%) |
|---|---|
| 2-[(2-isobutylamino)benzylsulfinyl]-imidazole (Example No. 10) | 97.2 |
| 2-[(5-methyl-2-methylamino)benzyl-sulfinyl]imidazole (Example No. 14) | 90.8 |
| 2-[(2-ethylamino)benzylsulfinyl]-imidazole (Example No. 25) | 87.5 |

(b) Pig gastric mucosa

Gastric acid secretory cells of a pig gastric mucosa were isolated in the same manner as in the test for rabbit gastric mucosa. A vesicle containing H$^+$ + K$^+$ ATPase was prepared by centrifuging the cells in Ficoll of discontinuous density gradient. The enzyme and each test compound were incubated at 37° C. for 30 min. in a solution which contained 2 mM of a bisTRIS-acetate buffer (pH 5.5). To the resulting mixture were added a solution of 37.5 mM of bisTRIS-acetate buffer solution (pH 7.4), 2 mM of magnesium chloride, 2 mM of ATP and 5 mM of potassium chloride, and the mixture was then heated to 37° C. for 10 min. for performing a reaction. The reaction was terminated by addition of 5% trichloroacetic acid solution, and an inorganic phosphorus liberated was quantitatively measured by Fiske-Subbarow method. The ATPase activity was determined from the obtained inorganic phosphorus value.

The above procedure was repeated except for not using potassium chloride to determine an ATPase activity in the absence of potassium chloride.

The desired K$^{30}$-dependent ATPase activity was calculated by subtracting the ATPase activity value determined in the absence of KCl from the ATPase activity value determined in the presence of KCl.

The results are set forth in Table 3.

TABLE 3

| Tested Compound (Example No.) | H$^+$ + K$^+$ ATPase inhibitory action (IC$_{50}$) ($10^{-6}$ M) |
|---|---|
| 2-(2-methylaminobeyzylsulfinyl)-4,5,6,7-tetrahydro-1H-benzimidazole (Example No. 2) | 1.8 |
| 2-(2-methylaminobenzylsulfinyl)imidazole (Example No. 8) | 2.8 |

(2) Inhibitory action against the secretion of gastric acid (Test I)

Male Donryu rats having a body weight of 200 to 250 g were fasted (while allowing free access to water) for 24 hrs. in accordance with the conventional method [Shay, H. et al, Gastroenterology, 5, 43–61 (1945)]. Under ether anesthesia the pylorus was ligated and each test compound was administered intraduodenally. Four hours later, each rat was killed and the stomach was removed to collect the gastric juice. The inhibitory action was determined by comparing the acid output which was determined by titration to pH 7.0 with 0.1-N NaOH by means of an automatic titrator, with the corresponding value of control rat prepared in the same manner except that a vehicle alone was administered.

The results are set forth in Table 4.

TABLE 4

| Tested compound | Dose (mg/kg) | Suppresive action (%) |
|---|---|---|
| 2-[(2-isobutylamino)benzylsulfinyl]-imidazole (Example No. 10) | 10 | 56.2 |
| | 30 | 87.0 |
| 2-[(5-methyl-2-methylamino)benzylsulfinyl]imidazole (Example No. 14) | 10 | 82.2 |
| | 30 | 98.6 |
| 2-[(2-ethylamino)benzylsulfinyl]-imidazole (Example No. 25) | 10 | 74.0 |
| | 30 | 93.3 |
| 2-[(2-isobutylamino-5-methoxy)benzylsulfinyl]imidazole (Example No. 29) | 10 | 30.8 |
| | 30 | 89.0 |
| 2-[(2-methyl-6-methylamino)benzylsulfinyl]imidazole (Example No. 33) | 10 | 92.9 |
| | 30 | 91.4 |
| 2-[(2-isobutylamino-6-methyl)benzylsulfinyl]imidazole (Example No. 45) | 10 | 86.8 |
| | 30 | 90.3 |

Remarks: Suppresive action: On secreatin of gastic acid (3) Inhibitory action against the secretion of gastric acid (Test II)

Heidenhain pouch dogs produced from male beagle dogs were fasted. To the dogs were then administered intarvenously histamine hydrochloride (gastric juice secretion inducing agent) continuously at a dose of 160 ug/kg/hr. The gastric juice was collected at an interval of 15 min. to measure the amount of gastric juice and acid output to determine an acid secretion amount (mEq/15 min).

The test compound was intravenously administered to the dogs at one hour after the initiation of histamine administration.

The inhibitory action was determined by comparing the acid secretion amount, with the corresponding amount of a control dog prepared in the same manner except that a vehicle alone was administered.

The results are set forth in Table 5.

TABLE 5

| Tested compound | Dose (mg/kg) | Suppresive action (%) |
|---|---|---|
| 2-(2-methylaminobenzylsulfinyl)-4,5,6,7-tetrahydro-1H-benzimidazole (Example No. 2) | 3 | 53 |
| 2-[(2-isobutylamino)benzylthio]-imidazole (Example No. 9) | 3 | 11 |
| 2-[(2-isobutylamino)benzylsulfinyl]-imidazole (Example No. 10) | 3 | 81 |
| 2-[(5-methyl-2-methylamino)benzylsulfinyl]imidazole (Example No. 14) | 3 | 97 |
| 2-[(2-isopropylamino)benzylsulfinyl]-imidazole (Example No. 23) | 3 | 66 |
| 2-[(2-ethylamino)benzylsulfinyl]-imidazole (Example No. 25) | 3 | 80 |
| 2-[(2-benzylamino)benzylsulfinyl]-imidazole (Example No. 27) | 3 | 57 |
| 2-[(2-isobutylamino-5-methoxy)benzylsulfinyl]imidazole (Example No. 29) | 1 | 30 |
| | 3 | 81 |
| 2-[(2-methyl-6-methylamino)benzylsulfinyl]imidazole (Example No. 33) | 1 | 70 |
| 4-methyl-2-[(2-methylamino)benzylsulfinyl]imidazole (Example No. 37) | 3 | 50 |
| 2-[(2-isobutylamino-6-methoxy)benzylsulfinyl]imidazole (Example No. 41) | 1 | 66 |
| | 3 | 97 |
| 2-[(2-isobutylamino-6-methyl)benzylsulfinyl]imidazole (Example No. 45) | 1 | 82 |
| 2-[(2-isobutylamino-4-methyl)benzylsulfinyl]imidazole (Example No. 47) | 1 | 87 |

Remark: Suppresive action: On secreatin of gastic acid (4) Acute toxicity test

2-[(2-Isobutylamino)benzylsulfinyl]imidazole (Example No. 10) was orally administered to rats and beagle dogs at a dose of 45 mg/kg/day for two weeks. There was observed no noticeable change on the administer rats and dogs.

Further, it has been confirmed that the imidazole derivatives of the formula (I) are well absorbable by 0 animals such as dogs and rats when the imidazole derivatives are orally administered to show a high concentration in blood of the tested animals. Furthermore, it has been confirmed that the imidazole derivatives of the formula (I) hasvea cytoprotective action.

The compounds (I) of the present invention can be administered either orally or parenterally. Preparation forms for oral administration may be, for example, tablets, capsules, powder, granules syrup and the like. Preparation forms for parenteral administration may be injectable preparations and the like. For the formulation of these preparations, excipients, disintegrants, binders, lubricants, pigments, diluents and the like which are commonly employed in the art may be used. The excipients may include dextrose, lactose and the like. Starch, carboxymethylcellulose calcium and the like may be used as the disintegrants. Magnesium stearate, talc and the like may be used as the lubricants. The binders may be hydroxypropylcellulose, gelatin, polyvinylpyrrolidone and the like.

The dose may usually be about 1 mg/day to 50 mg/day in the case of an injectable preparation and about 10 mg/day to 500 mg/day in the case of oral administration, both for an adult. The dose may be either increased or decreased depending on the age and other conditions.

Examples of the preparation of the imidazole derivatives of the formula (I) are given below.

EXAMPLE 1

Preparation of 2-(2-methylaminobenzylthio)-4,5,6,7-tetrahydro-1H-benzimidazole

To a suspension of 1.3 g (9 mmol) of 2-mercapto-4,5,6,7-tetrahydro-1H-benzimidazole in 20 ml of ethanol was added 1.35 g (7 mmol) of 2-methylaminobenzyl chloride hydrochloride for a period of 15 min. The solvent was distilled off, and the residue was shaken sufficiently with a combination of 1N aqueous sodium hydroxide and chloroform for performing extraction. The organic portion was taken out and then dried over anhydrous sodium sulfate. Chloroform was distilled off, and the residue was crystallized from ether/hexane to give 1.02 g of the desired compound as a pale brown crystalline product, yield 53%.

IR$\nu$(KBr): cm$^{-1-1}$
3390, 2910, 2840, 1605, 1580, 1510, 1385, 1310, 1170. 1000, 740

$^1$H—NMR (CDCl$_3$):$\delta$
1.6–2.0 (m, 4H), 2.3–2.8 (m, 4H), 2.80 (s, 3H), 4.13 (s, 2H), 6.4–7.3 (m, 4H)

EXAMPLE 2

Preparation of 2-(2-methylaminobenzylsulfinyl)-4,5,6,7-tetrahydro-1H-benzimidazole To a solution of 1.20 g (4 mmol) of 2-(2-methylaminobenzylthio)-4,5,6,7-tetrahydro-1H-benzimidazole in chloroform was added under chilling with ice 0.85 g (4 mmol) of 80% m-chloroperbenzoic acid for 20 min. The 30 mixture was then stirred for 15 min. The chloroform portion was washed with a saturated aqueous NaHCO$_3$ solution. The chloroform portion was then extracted with two portions of diluted aqueous NaOH solution. The aqueous extracts were combined, and an excess amount of aqueous NH$_4$Cl was added to the combined extracts to precipitate a crystalline product. The crystalline products were collected by filtration and sufficiently washed. The thus obtained crude crystalline product was recrystallized from dichloromethane/hexane to give 0.32 g of the desired compound as a white crystalline product, yield 25%.

IR$\nu$(KBr): cm$^{-1}$
3370, 3200, 2930, 1600, 1590, 1580, 1520, 1420, 1310, 1170, 1040, 735

$^1$H—NMR (CDCl$_3$—CD$_3$OD):δ
1.6–2.1 (m, 4H), 2.4–2.8 (m, 4H), 2.78 (s, 3H), 4.22 (d, 1H, J=14Hz), 4.40 (d, 1H, J=14Hz), 6.4–7.3 (m, 4H)
M.p.: 142°–144° C. (decomp.)

EXAMPLE 3

Preparation of 2-(2-dimethylaminobenzylthio)-4,5,6,7-tetrahydro-1H-benzimidazole To a suspension of 1.55 g (10 mmol) of 2-mercapto-4,5,6,7-tetrahydro-1H-benzimidazole in 20 ml of ethanol was added 1.81 g (8.8 mmol) of 2-dimethylaminobenzyl chloride hydrochloride for a period of 10 min. The mixture was then stirred for 30 min. Thus precipitated crystalline product was collected by filtration and washed successively with ethanol and hexane to give 2.16 g of a pale brown crystalline product. The obtained crystalline product was shaken with a combination of chloroform and aqueous NaHCO$_3$ for performing extraction. The chloroform portion was taken out and dried over anhydrous sodium sulfate. Chloroform was distilled off, and the residue was crystallized from diethyl ether/hexane. The crystalline residue was collected by filtration to give 1.44 g of the desired compound as a white crystalline product, yield 57%.

IR$\nu$(KBr): cm$^{-1}$
2930, 2850, 2820, 2780, 1490, 1445, 1390, 1000, 945, 755

$^1$H—NMR (CDCl$_3$):δ
1.6–2.0 (m, 4H), 2.3–2.8 (m, 4H), 2.75 (s, 6H), 4.23 (s, 2H), 6.8–7.4 (m, 4H)

EXAMPLE 4

Preparation of 2-(2-dimethylaminobenzylsulfinyl)-4,5,6,7-tetrahydro-1H-benzimidazole To a solution of 0.70 g (2.4 mmol) of 2-(2-dimethylaminobenzylthio)-4,5,6,7-tetrahydro-1H-benzimidazole in 7 ml of chloroform was added under chilling with ice 0.53 g (2.4 mmol) of 80% m-chloroperbenzoic acid for 10 min. To the resulting mixture were added chloroform and aqueous NaHCO$_3$. The chloroform portion was taken out, and then subjected to extraction using six portions of 1N aqueous NaOH. To the aqueous NaOH portion was added an excess amount of aqueous NH$_4$Cl to separate an oil out of the solution. The oil was then extracted with chloroform and dried over anhydrous sodium sulfate. Chloroform was distilled off, and the residue was crystallized from diethyl ether/hexane. The obtained crystalline products were collected by filtration and dried under reduced pressure to give 0.26 g of the desired compound as a white crystalline product, yield 35%.

IR$\nu$(KBr): cm$^{-1}$
3225, 2825, 1590, 1490, 1110, 1040, 1030, 755

$^1$H—NMR (CDCl$_3$):δ
1.6–2.0 (m, 4H), 2.3–2.9 (m, 4H), 2.65 (s, 6H), 4.38 and 4.70 (each d, 1Hx2, J=13Hz), 6.8–7.4 (m, 4H)
M.p.: 103°–106° C. (decomp.)

EXAMPLE 5

Preparation of 2-(2-aminobenzylthio)-4,5,6,7-tetrahydro-1H-benzimidazole

To a suspension of 1.5 g (purity 75%, 7.3 mmol) of 2-mercapto-4,5,6,7-tetrahydro-1H-benzimidazole in 15 ml of ethanol was added 1.3 g (7.3 mmol) of 2-aminobenzyl chloride hydrochloride, and the mixture was stirred for 2 hrs. at room temperature. Ethanol was distilled off under reduced pressure at room temperature. The residue was made alkaline by addition of saturated aqueous sodium hydrogencarbonate and then extracted with 40 ml of chloroform. The chloroform portion was washed with 10 ml of 0.2N NaOH and then with saturated aqueous sodium chloride. The washed chloroform portion was dried over anhydrous sodium sulfate and placed under reduced pressure to distill off the solvent. The residue was purified by silica gel column chromatography using chloroform-methanol to give 1.35 g of the desired compound as a pale yellow oil, yield 71.4%.

$^1$H—NMR (CDCl$_3$):δ
1.4–2.0 (m, 4H), 2.2–2.8 (m, 4H), 4.11 (s, 2H), 5.5 (br, 2H), 6.4–7.2 (m, 4H)

EXAMPLE 6

Preparation of 2-(2-aminobenzylsulfinyl)-4,5,6,7-tetrahydro-1H-benzimidazole To a solution of 1.3 g (5.0 mmol) of 2-(2-aminobenzylthio)-4,5,6,7-tetrahydro-1H-benzimidazole in 13 ml of chloroform was added under stirring and chilling with ice (5°–10° C.) 1.08 g (5.0 mmol) of 80% m-chloroperbenzoic acid for approx. 15 min. The mixture was further stirred for 15 min., and to the mixture was added saturated aqueous sodium hydrogencarbonate solution. Thus precipitated solid was collected by filtration and washed with two portions of water and one portion of acetonitrile. There was obtained 590 mg of a crude product. The chloroform portion of the mother liquor was taken out and subjected to extraction using 10 ml of 0.2N aqueous NaOH. The aqueous alkaline solution was made ammonia alkaline by addition of 20% aqueous NH$_4$Cl to precipitate a crystalline product. The crystalline product was collected and washed successively with two portions of water and one portion of acetonitrile to give 130 mg of a crude product. The crude products were combined and dissolved in 30 ml of 0.5N aqueous NaOH. The aqueous solution was washed with three portions of chloroform and then made ammonia-alkaline by addition of 20% aqueous NH₄Cl to precipitate a crystalline product. The obtained product was washed successively with two portions of water, one portion of acetonitrile and one portion of diethyl ether and then dried under reduced pressure at 35° C. for 8 hrs. to 624 mg of the desired compound as a white crystalline product, yield 45.4%.

IR$\nu$(KBr): cm$^{-1}$
3220, 3170, 1590, 1575, 1490, 1420, 1270, 1050, 1025, 740
$^1$H—NMR (DMSO-d₆):δ
2.5-3.0 (m, 4H), 3.2-3.8 (m, 4H), 4.37 (s, 2H), 5.16 (br, 2H), 6.3-7.2 (m, 4H), 12.7 (br, 1H)
M.p.: 178°-180° C. (decomp.)

EXAMPLE 7

Preparation of 2-(2-methylaminobenzylthio)imidazole

To a solution of 693 mg (6.9 mmol) of 2-mercaptoimidazole in 26 ml of ethanol was added 1.33 g (6.9 mmol) of 2-methylaminobenzyl chloride hydrochloride, and the mixture was stirred for 15 min. at room temperature. Ethanol was distilled off under reduced pressure. The residue was made alkaline by addition of saturated aqueous sodium hydrogencarbonate and then to the alkaline solution was added 20 ml of water to precipitate a crystalline product. The product was collected by filtration and washed successively with two portions of water and each one portion of chilled ethanol and ether to give 990 mg of the desired compound as a white crystalline powder, yield 05.5 %.

$^1$H—NMR (CD₃OD):δ
2.84 (s, 3H), 4.10 (s, 2H), 6.3-7.2 (m, 4H), 7.0 (s, 2H)

EXAMPLE 8

Preparation of 2-(2-methylaminobenzylsulfinyl)imidazole

To a solution of 900 mg (4.11 mmol) of 2-(2-methylaminobenzylthio)imidazole in a mixture of 40 ml of chloroform and 10 ml of methanol was portionwise added under chilling with ice 880 mg (4.11 mmol, purity 80%) of m-chloroperbenzoic acid. The mixture was then stirred for 30 min. To the stirred mixture was added a saturated aqueous sodium hydrogencarbonate. The resulting aqueous solution was subjected to extraction with 50 ml of chloroform. The chloroform portion was taken out and the subjected to extraction with three portions of 10 ml of 0.1N aqueous NaOH and one portion of 20 ml of 0.1N aqueous NaOH to transfer a product into the aqueous fractions. The last three aqueous fractions were combined and made ammonia-alkaline by addition of 20% aqueous ammonium chloride to precipitate a crystalline product. The product was collected, washed sufficiently with water and dried under reduced pressure at room temperature to give 637 mg of the desired compound as a pale yellow crystalline product, yield 66%.

IR$\nu$KBr): cm$^{-1}$
3370, 1605, 1580, 1520, 1465, 1310, 1040, 745
$^1$H—NMR (DMSO-d₆):δ
2.67 (m, 3H), 4.37 and 4.52 (each d, 2H, J=14Hz), 5.60 (br. 1H), 6.2-7.6 (m, 6H), 13.0 (br, s, 1H)
M.p.: 168° C. (decomp.)

EXAMPLE 9

Preparation of 2-[(2-isobutylamino)benzylthio]imidazole

To a solution of 427 mg of 2-mercaptoimidazole in 5 ml of ethanol was added at room temperature 1.0 g of 2-isobutylaminobenzyl chloride hydrochloride for approx. 5 min. Thus obtained homogeneous solution was stirred for 1 hr. at room temperature. Ethanol was distilled off under reduced pressure at a temperature below 40° C. To the residue were added a small amount of water and saturated aqueous sodium hydrogencarbonate. The aqueous solution was then subjected to extraction using chloroform. The chloroform portion was dried over anhydrous sodium sulfate and placed under reduced pressure to distill off the solvent. There was obtained 1.05 g of the desired compound as a white crystalline powder, yield 94%.

IR$\nu$(KBr): cm$^{-1}$
3390, 2950, 1605, 1515, 1460, 1420, 1315, 1100, 750
$^1$H—NMR (CDCl₃)δ
0.88 (d, 6H, J=7Hz), 1.84 (m, 1H), 2.84 (d, 2H, J=7Hz), 4.12 (s, 2H), 6.2-7.1 (m, 6H)

EXAMPLE 10

Preparation of 2-[(2-isobutylamino)benzylsulfinyl]imidazole

To a mixture of 1 g of 2-[(2-isobutylamino)benzylthio]imidazole, 40 ml of chloroform and 10 ml of methanol was portionwise added under chilling with ice an equivalent molar amount of m-chloroperbenzoic acid. The mixture was stirred to perform a reaction. Termination of the reaction was confirmed by means of TLC (thin layer chromatography). Subsequently, the reaction mixture was made alkaline by addition of saturated aqueous sodium hydrogencarbonate and subjected to extraction using chloroform. The chloroform extract was shaken successively with three portions of 10 ml of 0.1N aqueous NaOH and one portion of 20 ml of 0.1N aqueous NaOH to transfer the reaction product into the aqueous fractions. Each of the four fractions was made ammonia-alkaline by addition of 20% aqueous ammonium chloride. A precipitate deposited from each fraction was collected by filtration, washed sufficiently with ether, and dried to give 0.6 g of the desired compound as a white crystalline product, yield 56.5%.

IR$\nu$(KBr): cm$^{-1}$
3360, 3340, 3160, 2950, 1600, 1580, 1515, 1465, 1315, 1020, 750
$^1$H—NMR (CDCl₃/CD₃OD=1/1 vol/vol):δ
1.02 (d, 6H, J=7Hz), 1.94 (m, 1H), 2.90 (d, 2H, J=7Hz). 4.32 (d. 1H, J=13Hz), 4.54 (d. 1H, j=13Hz). 6.4-7.3 (m, 4H), 7.24 (s, 2H)
M.p.: 132°-133° C. (decomp.)

EXAMPLE 11

Preparation of 2-[(2-dimethylamino)benzylthio]imidazole

To a solution of 1214 g of 2-mercaptoimidazole in 12 ml of ethanol was added at room temperature 2.5 g of 2-dimethylaminobenzyl chloride hydrochloride for approx. 5 min. Thus obtained homogeneous solution was stirred for 1 hr. at room temperature. Ethanol was distilled off under reduced pressure at a temperature below 40° C. To the residue were added 10 ml of water and a saturated aqueous sodium hydrogencarbonate. The aqueous solution was then subjected to extraction using chloroform. The chloroform portion was dried over anhydrous sodium sulfate and placed under reduced pressure to distill off the solvent. After the residue was allowed to stand for one day, there was obtained 2.35 g of the desired compound as a white powder, yield 84%.

IR$\nu$(KBr) cm$^{-1}$ 1495, 1450, 1415, 1330, 1190, 1155, 1100, 1050, 950, 770, 760

¹H—NMR (CDCl₃):δ
2.60 (s, 6H), 4.22 (s, 2H), 6.7-7.3 (m, 6H)
M.p.: 73°-76° C.

EXAMPLE 12

Preparation of 2-[(2-dimethylamino)benzylsulfinyl]imidazole

To a solution of 2.2 g of 2-[(2-dimethylamino)benzylthio]imidazole in 50 ml of chloroform was portionwise added under chilling with ice an equivalent molar amount of m-chloroperbenzoic acid. The mixture was stirred to perform a reaction. Termination of the reaction was confirmed by means of TLC. Subsequently, the reaction mixture was made alkaline by addition of saturated aqueous sodium hydrogen carbonate and subjected to extraction using chloroform. The chloroform extract was shaken successively with three portions of 10 ml of 0.1N aqueous NaOH and one portion of 20 ml of 0.1N aqueous NaOH to transfer the reaction product into the aqueous fractions. Each of the four fractions was made ammonia-alkaline by addition of 20% aqueous ammonium chloride. A precipitate deposited from each fraction was collected by filtration, washed sufficiently with ether, and dried to give 1.03 g of the desired compound as a white crystalline powder, yield 43.8%.

IRν(KBr): cm⁻¹
3050, 2970, 2890, 2800, 1490, 1105, 1095, 1005, 940, 780, 765, 510

¹H—NMR (CDCl₃/CD₃OD=1/1 vol/vol):δ
2.66 (s, 6H), 4.50 (d, 1H, J=12Hz), 4.73 (d, 1H, J=12Hz), 6.8-7.4 (m, 4H), 7.22
M.P.: 115°-117° C. (decomp.)

EXAMPLE 13

Preparation of 2-[(5-methyl-2-methylamino)benzylthio]imidazole a) 5-Methyl-2-methylaminobenzyl chloride hydrochloride Ethyl 2-amino-5-methylbenzoate was treated with dimethylsulfuric acid to give a N-methylated product. The N-methylated product was reduced using lithium aluminum hydride to give 5-methyl-2-methylaminobenzyl alcohol. The obtained alcohol was reacted with thionyl chloride in benzene to give the desired compound, yield 22% (based on the amount of the starting benzoate).

b) 2[(5-Methyl-2-methylamino)benzylthio]imidazole

To a solution of 0.7 g of 2-mercaptoimidazole in 10 ml of ethanol was portionwise added at room temperature 1.44 g of 5-methyl-2methylaminobenzyl chloride hydrochloride. The obtained homogeneous solution was stirred for one hr. at room temperature. Ethanol was distilled off under reduced pressured at a temperature below 40° C. To the residue were successively added 40 ml of water and saturated aqueous sodium hydrogencarbonate. The aqueous solution was then subjected to extraction using chloroform. The chloroform extract was dried over anhydrous sodium sulfate and concentrated to give 1.456 g of the desired compound as a pale yellow crystalline product, yield 84.6%.

IR (KBr): cm⁻¹
3430, 1520, 1420, 1100, 965, 805, 760

¹H—NMR (CDCl₃):δ
2.16 (s, 3H), 2.77 (s, 3H), 5.13 (s, 2H), 5.95 (br, 1H), 6.3-7.2 (m, 5H)
M.p. : 113°-118° C.

EXAMPLE 14

Preparation of 2-[(5-methyl-2-methylamino)benzylsulfinyl]imidazole

To a solution of 1.45 g of 2-[(5-methyl-2-methylamino)benzylthio]imidazole in a mixture of 40 ml of chloroform and 10 ml of methanol was portionwise added under chilling with ice an equivalent molar amount of m-chloroperbenzoic acid. The mixture was stirred to perform a reaction. Termination of the reaction was confirmed by means of TLC. Subsequently, the reaction mixture was made alkaline by addition of saturated aqueous sodium hydrogencarbonate and subjected to extraction using chloroform. The chloroform extract was shaken successively with three portions of 10 ml of 0.1N aqueous NaOH and one portion of 20 ml of 0.1N aqueous NaOH to transfer the reaction product into the aqueous fractions. Each of the four fractions was made ammonia-alkaline by addition of 20% aqueous ammonium chloride. A precipitate deposited from each fraction was collected by filtration, washed sufficiently with ether, and dried to give 0.8 g of the desired compound as a white crystalline product, yield 51.6%.

IRν(KBr): cm⁻¹
3400, 2070, 3000, 2890, 2800, 1520, 1310, 1095, 1005, 890, 805

¹H—NMR (CDCl₃/CD₃OD =1/1 vol/vol):δ
2.15 (s, 3H), 2.77 (s, 3H), 4.28 (d, 1H, J=14Hz), 4.46 (d, 1H, J=14Hz), 6.4-7.1 (m, 3H), 7.24 (s, 2H)
M.p.: 125°-128° C. (decomp.)

EXAMPLE 15

Preparation of 2-(2-aminobenzylthio)imidazole

To a solution of 1.5 g (15 mmol) of 2-mercaptoimidazole in 15 ml of ethanol was added at room temperature 2.66 g (15 mmol) of 2-aminobenzyl chloride hydrochloride. The mixture was then stirred for one hr. at room temperature. The obtained homogeneous solution was placed under reduced pressure at a temperature below 40° C. to distill off the solvent. To the residue were successively added water and saturated aqueous sodium hydrogencarbonate to precipitate a crystalline product. The product was collected by filtration, washed twice with water, and dried to give 2.5 g of the desired compound as a pale gray crystalline product, yield 80.9%.

¹H—NMR (CDCl₃/CD₃OD=2/1. vol/vol):δ
4.11 (s, 2H), 7.00 (s, 2H), 6.4-7.1 (m, 4H)

EXAMPLE 16

Preparation of 2-(2-aminobenzylsulfinyl)imidazole

To a solution of 2.5 g of 2-(2-aminobenzylthio)imidazole in a mixture of 25 ml of chloroform and 10 ml of methanol was dropwise added under stirring and under chilling with ice 2.6 g (12.1 mmol) of m-chloroperbenzoic acid. The mixture was further stirred for 15 min. Thus precipitated crystalline product was collected by filtration, washed twice with water and placed in 40 ml of saturated aqueous sodium hydrogencarbonate. The aqueous mixture was stirred, and then the crystalline product was collected by filtration. The obtained solid product was stirred in a mixture of 30 ml of chloroform and 10 ml of 1N aqueous NaOH. The aqueous portion was taken out and made ammonia-alkaline by addition of 20% aqueous ammonium chloride. The mixture was chilled after addition of sodium chloride, to give a crystalline precipitate. The precipitate was collected by filtration, washed successively with two portions of water and one portion of acetone, and dried under reduced pressure to give 340 mg of the desired compound as a pale brown crystalline powder, yield 12.7%.

IR$\nu$(KBr): cm$^{-1}$
3460, 3350, 1635, 1490, 1100, 1035, 900, 750

$^1$H—NMR (DMSO-d$_6$):$\delta$
4.44 (s, 2H), 5.16 (br, 2H), 6.2–7.1 (m, 4H), 7.26 (s, 2H), 13.0 (br, 1H)

M p 170°–172° C. (decomp.)

EXAMPLE 17

Preparation of 2-[(2-methylamino)benzylsulfinyl]imidazole

A mixture of 87.1 g of 2-[(2-methylamino)benzylthio]imidazole, 1,220 ml of dichloromethane, 1,220 ml of methanol, and 122 ml of acetic acid was stirred for 30 min. at room temperature to completely dissolve the imidazole in the mixture. The mixture was then chilled with ice to a temperature below 5° C. To the chilled mixture were successively added 109 ml of 35% aqueous hydrogen peroxide, 55 ml of water and 2.72 g of ammonium vanadate. The mixture was stirred for approx. 3 hrs. at a temperature between −3° C. and 3° C. for performing a reaction. After the reaction was complete, 2,100 ml of 10% aqueous sodium carbonate was added to the reaction mixture to precipitate a crystalline product. The mixture was then stirred for 30 min. The precipitated crystalline product was collected by filtration, washed successively with water and dichloromethane, and then suspended in a mixture of 300 ml of dichloromethane and 200 ml of aqueous sodium hydroxide (15.9 g/200 ml). The obtained suspension was stirred for 30 min. at room temperature. Insoluble crystals were removed by filtration, and the aqueous portion was taken out and washed with dichloromethane. Aqueous ammonium chloride (25.5 g/200 ml) was added to the above-obtained aqueous mixture to precipitate a crystalline product. The product was collected by filtration and washed with water to give 67.1 g of a pale brown crystalline product.

The obtained crystalline product (67.1 g) was suspended in 1,340 ml of acetone and heated under reflux of acetone. There was produced 60.8 g of a pale brown crystalline product. The produced product was dissolved in aqueous sodium hydroxide (12.4 % g/100 ml). To the resulting solution was dropwise added at room temperature aqueous ammonium chloride (19.9 g/400 ml) for a period of 45 min. The mixture was then stirred for 45 min. to precipitate a crystalline product. The product was collected by filtration and washed sufficiently with water to give 57.6 g of the desired compound as a pale brown crystalline powder, yield 61.6%.

EXAMPLE 18

Preparation of 2-[(2-isobutylamino-5-nitro)benzylthio]imidazole a) 2-Amino-5-nitrobenzyl alcohol To a suspension of 676 mg (17.9 mmol) of lithium aluminum hydride in 35 ml of dry tetrahydrofuran was dropwise added under stirring and chilling with ice (below 10° C.) a solution of 3.5 g (17.9 mmol) of methyl 5-nitroanthranylate in 50 ml of dry tetrahydrofuran for 15 min. The mixture was further stirred for 30 min. To the solution was dropwise added saturated aqueous sodium sulfate. Insolubles were removed by filtration. The filtrate was then placed under reduced pressure to distill off the solvent. There was obtained 2.76 g of the desired compound as a yellow crystalline product.

$^1$H—NMR (CDCl$_3$):$\delta$
4.57 (s, 2H), 0.68 (d, 1H, J=9Hz), 7.8–8.1 (m, 2H)

b) 1,2-Dihydro-2-isopropyl-6-nitro-4H-3,1-benzoxazine

To a solution of 2.5 g (14.9 mmol) of 2-amino-5-nitrobenzyl alcohol obtained in a) above and 4.3 g (59.6 mmol) of isobutyl aldehyde in 15 ml of tetrahydrofuran was added 1.2 g of anhydrous calcium chloride. The mixture was then stirred for 48 hrs. at room temperature. Insolubles were removed by filtration. The filtrate was placed under reduced pressure to distill off the solvent. The residue was crystallized by addition of hexane to give 2.86 g of the desired compound as a yellow crystalline product.

$^1$H—NMR CDCl$_3$):$\delta$
1.02 (d, 6H, J=7Hz), 1.6–2.0 (m, 1H), 4.48 (dd, 1H, J=2Hz, 5Hz), 4.80 (s, 2H), 4.94 (br, 1H), 6.48 (d, 1H, J=9Hz), 7.6–8.0 (m, 2H)

c) 2-Isobutylamino-5-nitrobenzyl alcohol

To a solution of 1.43 g (6.4 mmol) of 1,2-dihydro-2-isopropyl-6-nitro-4H−3,1-benzoxazine obtained in b) above in 14 ml of ethanol was added 486 mg (12.8 mmol) of sodium boron hydride. The mixture was then heated under reflux for 2 hrs. After the reaction was complete, 20% aqueous ammonium chloride was added to the reaction mixture under chilling with ice. The solution was treated with ether for extraction. The etheral extract was washed successively with water and saturated aqueous sodium chloride and dried over anhydrous sodium sulfate. The solvent was distilled off under reduced pressure to leave 1.23 g of the desired compound as a brown oil.

$^1$H—NMR (CDCl$_3$):$\delta$
1.00 (d, 6H, J=7Hz), 1.94 (m, 1H), 2.24 (br, 1H), 3.04 (t, 2H, J=7Hz), 4.64 (s, 2H), 5.86 (br, 1H), 6.48 (d, 1H, J=9Hz), 7.82 (d, 1H, J=2Hz), 7.96 (dd, 1H, J=2Hz, J=9Hz)

d) 2-[(2-Isobutylamino-5-nitro)benzylthio]imidazole

In a solution of 1 23 g (5.5 mmol) of 2-isobutylamino-5-nitrobenzyl alcohol in 10 ml of methylene chloride was dropwise added under chilling with ice a solution of 0.48 ml (0.5 mmol) of thionyl chloride in 3 ml of methylene chloride. The mixture was stirred for 15 min. at room temperature. The solvent was distilled off under reduced pressure. To the residue were added 20 ml of ethanol and 1.5 g (15 mmol) of 2-mercaptoimidazole. The mixture was then stirred for 2 hrs. at room temperature. Ethanol was distilled off under reduced pressure. The residue was extracted with ethyl acetate after addition of saturated aqueous sodium hydrogencarbonate. The extract was washed successively with water and saturated aqueous sodium chloride and dried over anhydrous sodium sulfate. The solvent was distilled off under reduced pressure. The residue was crystallized by addition of ether to give 1.40 g of the desired compound as a yellow crystalline product.

$^1$H—NMR (CDCl$_3$/CD$_3$OD=2/1, vol/vol):$\delta$ 1.00 (d, 6H, J=7Hz), 2.00 (m, 1H), 3.10 (d, 2H, J=7Hz), 4.24 (s, 2H), 6.57 (d, 1H, J=9Hz), 7.03 (s, 2H), 7.82 (d, 1H, J=2Hz), 7.98 (dd, 1H, J=2Hz, J=9Hz),

EXAMPLE 19

Preparation of 2-[(2-isobutylamino-5-nitro)benzylsulfinyl]imidazole

To a solution of 800 mg (2.61 mmol) of 2-[(2-isobutylamino-5-nitro)benzylthio]imidazole obtained in Example 18 in a mixture of 6 ml of methylene chloride, 6 ml of methanol and 0.6 ml of acetic acid were added under chilling with ice (to keep the inner temperature in a range of 2° to 5° C.) 1.3 ml of 35% aqueous hydrogen peroxide and 20 ml of ammonium methavanadate. The obtained mixture was then stirred for 1.5 hrs. at the same temperature. After the reaction was complete, the mixture was further stirred for 15 min. after addition of saturated aqueous sodium hydrogen carbonate, to give a crystalline precipitate. The precipitate was collected by filtration and washed with water. The crystalline precipitate was dissolved in a mixture of 50 ml of 6N aqueous NaOH and 50 ml of chloroform. The aqueous portion was taken out and made ammonia-alkaline by addition of 20% aqueous ammonium chloride to precipitate a crystalline product. The product was collected by filtration and washed successively with ethanol and ether. The product was dissolved in a mixture of 200 ml of chloroform and 100 ml of methanol. Insolubles were removed by filtration. The filtrate was placed under reduced pressure to distill off the solvent. The residue was crystallized by addition of ether to give 310 mg of the desired compound as a yellow crystalline product.

IR$\nu$(KBr): cm$^{-1}$
3300, 1605, 1590, 1495, 1325, 1310, 1285, 1100, 1025

$^1$H—NMR (DMSO-d$_6$):$\delta$
0.94 (d, 6H, J=7Hz), 1.92 (m, 1H), 3.02 (t, 2H, J=6Hz), 4.62 (s, 2H), 6.66 (d, 1H, J=9Hz), 7.0–7.2 (m, 1H), 7.27 (s, 2H), 7.65 (d, 1H, J=3Hz), 7.96 (dd, 1H, J=3Hz, J=9Hz), 13.1 (br, 1H)

M.p.: 215°–220° C. (decomp.)

EXAMPLE 20

Preparation of 2-[(4-chloro-2-isobutylamino)benzylthio]imidazole a) Methyl 4-chloroanthranilate A solution of 10.0 g (58 mmol) of 4-chloroanthranilic acid in 100 ml of methanol was heated under reflux, while gaseous hydrogen chloride was blown through the heated solution for 2.5 hrs. After the heating was terminated, methanol was distilled off. The residue was shaken with chloroform and aqueous sodium carbonate. The organic phase was taken out and dried over anhydrous sodium sulfate. Chloroform was distilled off under reduced pressure to leave 9.68 g of the desired compound as a residual pale brown crystalline product.

$^1$H—NMR (CDCl$_3$):$\delta$
3.86 (s, 3H), 5.76 (br, 2H), 6.58 (m, 1H), 6.65 (s, 1H), 7.76 (d, 1H, J=8Hz)

b) Methyl 4-chloro-2-(isobutylylamino)benzoate

To a solution of 9.68 g (52 mmol) of methyl 4-chloroanthranilate obtained in a) above in 15 ml of benzene were added 8.64% g of potassium carbonate and 6.67 g (63 mmol) of isobutyryl chloride. The mixture was heated under reflux for 1 hr. The mixture was mixed with water, and the benzene portion was taken out and dried over anhydrous sodium sulfate. Benzene was distilled off. The residue was crystallized by addition of hexane to give 9.85 g of the desired compound as a pale brown crystalline product.

$^1$H—NMR (CDCl$_3$):$\delta$
1.29 (d, 6H, J=7Hz), 2.62 (m, 1H), 3.93 (s, 3H), 7.02 (dd, 1H, J=2Hz, J=9Hz), 7.94 (d, 1H, J=9Hz), 8.86 (d, 1H, J=2Hz), 11.16 (br, 1H)

c) 4-Chloro-2-(isobutylamino)benzyl alcohol

To a suspension of 3.96 % (105 mmol) of lithium aluminum hydride in 200 ml of dry ether was dropwise added under chilling with ice for 15 min. a solution of 9.50 g (37 mmol) of methyl 4-chloro-2-(isobutyrylamino)benzoate obtained in b) above in a mixture of 20 ml of dry dichloromethane and 20 ml of dry ether. The mixture was then stirred for 30 min., and heated under reflux for 30 min. To the mixture was dropwise added under chilling with ice a saturated aqueous sodium sulfate. The organic portion was taken out by decantation, and dried over anhydrous sodium sulfate. The solvent was distilled off to leave 7.28 g of the desired compound as a residual colorless oil.

$^1$H—NMR (CDCl$_3$):$\delta$
0.09 (d, 6H, J=6Hz), 1.92 (m, 1H), 2.91 (d, 2H, J=6Hz), 4.58 (s, 2H), 6.3–7.0 (m, 3H)

d) 2-[(4-Chloro-2-isobutylamino)benzylthio]imidazole

To a solution of 7.28 g (34 mmol) of 4-chloro-(isobutylamino)benzyl alcohol obtained in c) above in 70 ml of methylene chloride was added under chilling with ice 3.2 ml (43.9 mmol) of thionyl chloride for 10 min. The mixture was then stirred for 15 min. The solvent was distilled off to leave a residue. The residue was stirred with a solution of 7.28 g (72.8 mmol) of 2-mercaptoimidazole in 100 ml of ethanol for 30 min. at room temperature. Ethanol was distilled off to leave a residue. The residue was shaken with chloroform and 10% aqueous sodium carbonate. The organic portion was taken out and dried over anhydrous sodium sulfate. Chloroform was distilled off to leave a residue. The residue was purified by silica gel column chromatography and crystallized from ether/hexane to give 6.90 g of the desired compound as a white crystalline powder.

$^1$H—NMR(CDCl$_3$/CD$_3$OD=1/1, vol/vol):$\delta$
1.01 (d, 6H, J=7Hz), 1.96 (m, 1H), 2.95 (d, 2H, J=7Hz), 4.12 (s, 2H), 6.46 (dd, 1H, J=2Hz, J=8Hz), 6.56 (d, 1H, J=2Hz), 6.80 (d, 1H, J=8Hz), 7.02 (s, 2H)

EXAMPLE 21

Preparation of 2-[(4-chloro-2-isobutylamino)benzylsulfinyl]imidazole

To a solution of 2.00 g (6.7 mmol) of 2-[(4-chloro2-isobutylamino)benzylthio]imidazole in a mixture of 20 ml of chloroform, 20 ml of methanol and 2.0 ml of acetic acid were added under chilling with ice 3.0 ml of 35% aqueous hydrogen peroxide and 45 mg of ammonium methavanadate. The mixture was stirred for 3 hrs. After the stirring was terminated, to the mixture was added aqueous sodium carbonate (5 g/50 ml). A crystalline product precipitated, was collected by filtration and washed successively with methylene chloride and water. The washed product was dissolved in 12 ml of 2N aqueous NaOH, and insolubles were removed by filtration. To the filtrate was added 30 ml of 1N aqueous ammonium chloride. A crystalline product precipitated. The precipitate was collected by filtration to give 1.50 g of the desired compound as a white crystalline powder.

IRν(KBr): cm⁻¹
3330, 2950, 2900, 1590, 1570, 1510, 1465, 1420, 1310, 1280, 1100, 1020, 745

¹H—NMR (DMSO-d₆):δ
0.95 (d, 6H, J=7Hz), 1.89 (m, 1H), 2.84 (br, 2H), 4.44 (d, 1H, J=13Hz), 4.60 (d, 1H, J=13Hz), 5.94 (br, 1H), 6.43 (dd, 1H, J=1Hz, J=8Hz), 6.49 (d, 1H, J=1Hz), 6.74 (d, 1H, J=8Hz), 6.9-7.5 (br, 2H)

M.p.: 173° C. (decomp.)

EXAMPLE 22

Preparation of 2-[(2-isopropylamino)benzylthio]imidazole

A solution of 2.0 g (12.1 mmol) of 2-(isopropylamino)-benzyl alcohol (which was prepared from 2-aminobenzyl alcohol and acetone in the manner described in Example 18-b) and -c)) in 20 ml of methylene chloride was dropwise added under chilling with ice a solution of 1.32 ml (18.1 mmol) of thionyl chloride in 5 ml of methylene chloride for approx. 15 min. The mixture was then stirred for 1 hr at the same temperature. The solvent was distilled off under reduced pressure at a temperature below 40° C. To the residue were added 2.42 g (24.2 mmol) of 2-mercaptoimidazole and 20 ml of ethanol, and the mixture was stirred for 1 hr. at room temperature. The solvent was distilled off under reduced pressure. The residue was made weak alkaline by successive addition of 50 ml of water and 1N aqueous NaOH and extracted with chloroform. The organic portion was washed successively with water and saturated aqueous sodium chloride and dried over anhydrous sodium sulfate. The solvent was distilled off under reduced pressure to leave a residue. The residue was then crystallized from ether/hexane (1/3) to give 1.70 g of the desired compound as a brown crystalline powder.

¹H—NMR CDCl₃):δ
1.19 (d, 6H, J=6Hz), 3.4-3.8 (m, 1H), 4.17 (s, 2H), 6.3-7.2 (m, 4H), 7.02 (s, 2H)

EXAMPLE 23

Preparation of 2-[(2-isopropylamino)benzylsulfinyl]imidazole

To a solution of 1.75 g (7.09 mmol) of 2-[(2-isopropylamino)benzylthio]imidazole (which was prepared in Example 22) in a mixture of 16 ml of methylene chloride, 16 ml of methanol and 1.6 ml of acetic acid were added under chilling with ice (to keep the inner temperature at a temperature in the range of 2°-5° C.) 3.2 ml of 35% aqueous hydrogen peroxide and 50 mg of ammonium methavanadate. The mixture was stirred for 3.0 hrs. at the same temperature. After the stirring was terminated, the mixture was subjected to extraction using chloroform, after addition of saturated aqueous sodium hydrogencarbonate. The chloroform portion was subjected to extraction using one portion of 15 ml of 0.5N aqueous NaOH and two portions of 15 ml of 1N aqueous NaOH. The obtained 1N-aqueous NaOH extracts were combined, made ammonia-alkaline by addition of 20% aqueous ammonium chloride, and subjected to extraction using chloroform. The organic extract was washed with saturated aqueous sodium chloride and dried over anhydrous sodium sulfate. The solvent was distilled off under reduced pressure. The residue was crystallized by addition of ether to give 1.13 g of the desired compound as a pale brown crystalline powder.

IRν(KBr): cm⁻¹
3375, 2970, 1600, 1580, 1515, 1440, 1305, 1175, 1100, 1040, 750, 500

¹H—NMR (CDCl₃/CD₃OD=3/1, vol/vol):δ
1.21 (d, 6H, J=6Hz), 3.60 (m, 1H), 4.24 and 4.51 (each d, 2H, J=14Hz), 6.4-7.3 (m, 4H), 7.21 (s, 2H)

M.p.: 130-132° C. (decomp.)

EXAMPLE 24

Preparation of 2-[(2-ethylamino)benzylthio]imidazole

To a solution of 6.4 g (42 mmol) of 2-ethylaminobenzyl alcohol (prepared by reducing methyl 2-acetamidobenzoate with lithium aluminum hydride) in 90 ml of dry benzene was dropwise added under chilling with ice 4.6 ml (62 mmol) of thionyl chloride in 90 ml of dry benzene for 20 min. The mixture was stirred for 1 hr. at room temperature and subsequently 20 min. at 50° C. The solvent was distilled off under reduced pressure at a temperature below 50° C. to leave 7.7 g of 2-ethylaminobenzyl chloride hydrochloride as a brown oil. The obtained hydrochloride (7.7 g, 35 mmol) was portionwise added to a solution of 3.7 g (37 mmol) of 2-mercaptoimidazole in 60 ml of ethanol. The mixture was then stirred for 1 hr. Ethanol was distilled off under reduced pressure at a temperature below 40° C. The residue was shaken with saturated aqueous sodium hydrogencarbonate and chloroform. The chloroform portion was taken out and dried over anhydrous sodium sulfate. The solvent was distilled off under reduced pressure. The residue was crystallized by addition of ether to give 4.78 g of the desired compound as a pale yellow crystalline powder.

¹H—NMR (CDCl₃):δ
1.25 (t, 3H, J=7Hz), 3.13 (q, 2H, J=7Hz), 4.17 (s, 2H), 6.3-7.3 (m, 4H), 7.03 (s, 2H)

EXAMPLE 25

Preparation of 2-[(2-ethylamino)benzylsulfinyl]imidazole

To a solution of 7.3 g (31.3 mmol) of 2-[(2-ethylamino)benzylthio]imidazole (which was prepared in the same manner as in Example 24) in a mixture of 80 ml of methylene chloride and 80 ml of methanol were added under chilling with ice (to keep the inner temperature at a temperature in the range of 2°-5° C.) 12 ml of 35% aqueous hydrogen peroxide and 191 mg of ammonium methavanadate. The mixture was stirred for 2.5 hrs. at the same temperature. After the stirring was terminated, the mixture was subjected to extraction using 50 ml of methylene chloride, after adding saturated aqueous sodium hydrogencarbonate and confirming that the mixture was made alkaline. The organic extract was then subjected to extraction using two portions of 30 ml of 1N aqueous NaOH. The extracts were combined and made ammonia-alkaline by addition of 20% aqueous ammonium chloride to give a precipitate. The obtained solid precipitate was extracted with chloroform. The extract was washed with saturated aqueous sodium chloride and dried over anhydrous sodium sulfate. The solvent was distilled off under reduced pressure. The residue was crystallized by addition of 60 ml of ethanol to give 6.4 g of the desired compound as a pale yellow crystalline product.

IRν(KBr): cm⁻¹
3380, 3070, 2970, 2900, 1605, 1580, 1520, 1310, 1090, 995, 885, 745, 500

¹H—NMR (CDCl₃/CD₃OD=1/1, vol/vol):δ

1.27 (t, 3H, J=7Hz), 3.11 (q, 2H, J=7Hz), 4.32 (d, 1H, J=14Hz), 4.52 (d, 1H, J=14Hz) 6.4-7.3 (m, 4H), 7.23 (s, 2H)

M.p.: 145-146.5° C. (decomp.)

EXAMPLE 26

Preparation of 2-[(2-benzylamino)benzylthio]imidazole

The desired compound was prepared in the same manner as in Example 9.

$^1$H—NMR (CDCl$_3$):δ
4.23 (s, 2H), 4.36 (s, 2H), 6.4-7.6 (m, 11H)

EXAMPLE 27

Preparation of 2-[(2-benzylamino)benzylsulfinyl]imidazole

The desired compound was prepared from 2-[(2-benzylamino)benzylthio]imidazole obtained in Example 26 in the same manner as in Example 10.

IRν(KBr): cm$^{-1}$
3410, 3150, 1610, 1590, 1520, 1450, 1320, 1030, 745

$^1$H—NMR (DMSO-d$_6$):δ
4.32 603 (d, 2H, J=6Hz), 4.57 (s, 2H), 6.2-7.5 (m, 1H)

M.p.: 135°-138° C. (decomp.)

EXAMPLE 28

Preparation of 2-[(2-isobutylamino-5-methoxy)benzylthio]imidazole

The desired compound was prepared in the form of a pale brown crystalline powder in the same manner as in Example 9.

$^1$H—NMR (CDCl$_3$/CD$_3$OD=1/1, vol/vol):δ
0.99 (d, 6H, J=7Hz), 1.92 (m, 1H), 2.90 (d, 2H, J=7Hz), 3.66 (s, 3H), 4.17 (s, 2H), 6.4-6.8 (m, 3H), 7.03 (br, 2H)

EXAMPLE 29

Preparation of 2-[(2-isobutylamino-5-methoxy)benzylsulfinyl]imidazole

The desired compound was prepared in the form of a pale brown crystalline powder from 2-[(2-isobutylamino-5-methoxy)benzylthio]imidazole obtained in Example 28 in the same manner as in Example 19.

IRν(KBr): cm$^{-1}$
3330, 2950, 2900, 1510, 1470, 1420, 1290, 1235, 1040, 1020

$^1$H—NMR (CDCl$_3$/CD$_3$OD=1/1 vol/vol):δ
1.02 (d, 6H, J=7Hz), 1.92 (m, 1H), 2.84 (d, 2H, J=7Hz), 3.65 (s, 3H), 4.31 (d, 1H, J=13Hz), 4.58 (d, 1H, J=13Hz) 6.3-6.9 (m, 3H), 7.24 (s, 2H)

M.p.: 132°-134° C. (decomp.)

EXAMPLE 30

Preparation of 2-[(2,3-dimethoxy-6-isobutylamino)benzylthio]imidazole

The desired compound was prepared in the form of a white crystalline product in the same manner as in Example 9.

$^1$H—NMR CDCl$_3$):δ
0.99 (d, 6H, J=7Hz), 1.93 (m, 1H), 2.85 (d, 2H, J=7Hz), 3.78 (s, 3H), 3.84 (s, 3H), 4.32 (s, 2H), 6.33 (d, 1H, J=9Hz), 6.78 (d, 1H, J=9Hz), 7.01 (s, 2H)

EXAMPLE 31

Preparation of 2-[(2,3-dimethoxy-6-isobutylamino)benzylsulfinyl]imidazole

The desired compound was prepared in the form of a pale yellow crystalline powder from 2-[(2,3-dimethoxy-6-isobutylamino)benzylthio]imidazole obtained in Example 30 in the same manner as in Example 19.

IRν(KBr): cm$^{-1}$
3330, 3100, 2940, 2900, 2860, 2820, 1510, 1480, 1470, 1260, 1080, 1020, 770

$^1$H—NMR (CDCl$_3$/CD$_3$OD=1/1 vol/vol):δ
1.02 (d, 6H, J=7Hz), 1.92 (m, 1H), 2.82 (d, 2H, J=7Hz), 3.80 (s, 3H), 3.86 (s, 3H), 4.57 (s, 2H), 6.40 (d, 1H, J=9Hz) 6.90 (d, 1H, J=9Hz), 7.27 (s, 2H)

M.p.: 130°-132° C. (decomp.)

EXAMPLE 32

Preparation of 2-[(2-methyl-6-methylamino)benzylthio]imidazole

The desired compound was prepared in the form of a pale yellow crystalline powder in the same manner as in Example 9.

M.p.: 174°-177° C.

EXAMPLE 33

Preparation of 2-[(2-methyl-6-methylamino)benzylsulfinyl]imidazole

The desired compound was prepared in the form of a white crystalline product from 2-[(2-methyl-6-methylamino)benzylthio]imidazole obtained in Example 32 in the same manner as in Example 19.

IRν(KBr): cm$^{-1}$
3370, 2810, 1590, 1520, 1470, 1425, 1315, 1040, 770, 750

$^1$H—NMR (DMSO-d$_6$):δ
2.17 (s, 3H), 2.68 (d, 3H, J=5Hz), 4.32 (d, 1H, J=14Hz), 4.68 (d, 1H, J=14Hz) 5.46 (m, 1H), 6.2-7.2 (m, 3H), 7.30 (br, 2H)

M.p.: 152°-154° C. (decomp.)

EXAMPLE 34

Preparation of 3-[(2-isobutylamino-5-trifluoromethoxy)benzylthio]imidazole

The desired compound was prepared in the form of a white crystalline powder in the same manner as in Example 9.

$^1$H—NMR (CDCl$_3$):δ
0.98 (d, 6H, J=7Hz), 1.93 (m, 1H), 2.92 (d, 2H, J=7Hz), 4.17 (s, 2H), 4.80 (br, 1H), 6.54 (d, 1H, J=9Hz), 6.6-7.1 (m, 2H), 7.0 (s, 2H),

EXAMPLE 35

Preparation of 2-[(2-isobutylamino-5-trifluoromethoxy)benzylsulfinyl]imidazole

The desired compound was prepared in the form of a white crystalline powder from 2-[(2-isobutylamino-5-trifluoromethoxy)benzylthio]imidazole obtained in Example 34 in the same manner as in Example 19.

IRν(KBr): cm$^{-1}$
3370, 1520, 1470, 1245, 1220, 1160, 1105, 1030, 770

$^1$H—NMR (CDCl$_3$/CD$_3$OD=1/1 vol/vol):δ

1.02 (d, 6H, J=6Hz), 1.92 (m, 1H), 2.89 (d, 2H, J=7Hz), 4.28 and 4.52 (each d, 2H, J=14Hz), 6.4-7.1 (m, 3H), 7.23 (s, 2H)

M.p.: 141°-142° C. (decomp.)

EXAMPLE 36
Preparation of 4-methyl-2-[(2-methylamino)benzylthio]imidazole

The desired compound was prepared in the form of a brown oil in the same manner as in Example 9.

EXAMPLE 37
Preparation of 4-methyl-2[(2-methylamino)benzylsulfinyl]imidazole The desired compound was prepared in the form of a white crystalline product from 4-methyl-2-](2-methylamino)benzylthio]imidazole obtained in Example 36 in the same manner as in Example 19.

IR$\nu$(KBr): cm$^{-1}$
3400, 1605, 1520, 1310, 1005, 990, 890, 750

$^1$H—NMR (DMSO-d$_6$):$\delta$
2.19 (s, 3H), 2.69 (d, 3H, J=4Hz), 4.41 (s, 2H), 5.66 (br, 1H), 6.3-7.2 (m, 5H), 13.0 (br, 1H)

M.p.: 143°-146° C. (decomp.)

EXAMPLE 38
Preparation of 2-[(5-chloro-2-isobutylaminobenzylthio]imidazole

The desired compound was prepared in the form of a white crystalline product in the same manner as in Example 9.

$^1$H—NMR (CDCl$_3$):$\delta$
0.96 (d, 6H, J=6H), 1.92 (m, 1H), 2.89 (d, 2H, J=7Hz), 4.15 (s, 2H), 4.87 (br, 1H), 6.3-7.2 (m 3H), 7.04 (s, 2H)

EXAMPLE 39
Preparation of 2-[(5-chloro-2-isobutylaminobenzylsulfinyl]imidazole The desired compound was prepared in the form of a pale brown crystalline powder from 2-[(5-chloro-2-isobutylamino)benzylthio]imidazole obtained in Example 38 in the same manner as in Example 19.

IR$\nu$(KBr): cm$^{-1}$
3325, 2860, 1600, 1580, 1510, 1460, 1420, 1315, 1100, 1020, 875, 800, 750

$^1$H—NMR (DMSO-d$_6$):$\delta$
0.94 (d, 6H, J=7Hz), 1.87 (m, 1H), 2.83 (br, 2H), 4.52 (s, 2H), 5.76 (br, 1H) 6.4-7.2 (m, 3H), 7.29 (s, 2H)

M.p.: 151°-154° C. (decomp.)

EXAMPLE 40
Preparation of 2-[(2-isobutylamino-6-methoxy)benylthio]imidazole

The desired compound was prepared in the form of a white crystalline powder in the same manner as in Example 9.

$^1$H—NMR (CDCl$_3$):$\delta$
0.99 (d, 6H,J=7Hz), 1.94 (m, 1H), 2.91 (d, 2H, J=7Hz), 3.79 (s, 3H), 4.36 (s, 2H), 5.07 (br, 1H), 6.25 (d, 1H, J=8Hz), 6.28 (d, 1H, J=8Hz), 7.0-7.4 (m, 3H)

EXAMPLE 41
Preparation of 2-[(2-isobutylamino-6-methoxy)benzylsulfinyl]imidazole The desired compound was prepared in the form of a pale brown crystalline powder from 2-[(2-isobutylamino-6-methoxy)benzylthio]imidazole obtained in Example 40 in the same manner as in Example 19.

IR$\nu$(KBr): cm$^{-1}$
3360, 2950, 1600, 1585, 1480, 1470, 1260, 1250, 1160, 1100, 1020, 770

$^1$H—NMR (CDCl$_3$):$\delta$
0.97 (d, 6H, J=7Hz), 1.87 (m, 1H), 2.7-3.0 (br, 2H), 3.72 (s, 3H), 4.38 (d, 1H, J=13Hz), 4.79 (d, 1H, J=13Hz) 5.25 (br, 1H), 6.26 (d, 1H, J=8Hz), 6.33 (d, 1H, J=8Hz), 7.0-7.3 (m, 3H)

M.p.: 116° C. (decomp.)

EXAMPLE 42
Preparation of 2-[(5-fluoro-2-isobutylamino)benzylthio]imidazole

The desired compound was prepared in the form of a pale yellow crystalline product in the same manner as in Example 9.

$^1$H—NMR (CDCl$_3$):$\delta$
0.99 (d, 6H, J=7Hz), 1.92 (m, 1H), 2.89 (d, 2H, J=7Hz), 4.16 (s, 2H), 6.3-7.1 (m, SH), 7.05 (s, 2H)

EXAMPLE 43
Preparation of 2-[(5-fluoro-2-isobutylamino)benzylsulfinyl]imidazole The desired compound was prepared in the form of a white crystalline powder from 2-[(5-fluoro-2-isobutylamino)benzylthio]imidazole obtained in Example 42 in the same manner as in Example 19. $\nu$(KBr): cm$^{-1}$
3340, 3160, 2940, 1515, 1465, 1420, 1310, 1215, 1020, 960, 795, 755

$^1$H—NMR (CDCl$_3$/CD$_3$OD=1/1 vol/vol):$\delta$
1.02 (d, 6H, J=7Hz), 1.92 (m, 1H), 2.85 (d, 2H, J=7Hz), 4.31 (d, 1H, J=14Hz), 4.54 (d, 1H, J=14Hz), 6.4-7.0 (m, 3H), 7.25 (s, 2H)

M.p.: 150°-151° C. (decomp.)

EXAMPLE 44
Preparation of 2-[(2-isobutylamino-6-methyl)benzylthio]imidazole

The desired compound was prepared in the form of a pale brown crystalline product in the same manner as in Example 9.

$^1$H—NMR (CDCl$_3$):$\delta$
0.98 (d, 6H, J=7Hz), 1.93 (m, 1H), 2.18 (s, SH), 2.90 (d, 2H, J=7Hz), 4.27 (s, 2H), 6.49 (d, 2H, J=8Hz), 7.04 (t. 1H, J=8Hz), 7.04 (s, 2H)

EXAMPLE 45
Preparation of 2-[(2-isobutylamino-6-methyl)benzylulfinyl]imidazole The desired compound was prepared in the form of a white crystalline powder from 2-[(2-isobutylamino-6-methyl)benzylthio]imidazole obtained in Example 44 in the same manner as in Example 19.

IR$\nu$(KBr): cm$^{-1}$
3350, 2950, 2900, 2870, 1590, 1520, 1480, 1470, 1420, 1320, 1100, 1020, 770, 750

$^1$H—NMR (CDCl$_3$/CD$_3$0D=1/1 vol/vol):$\delta$
1.02 (d, 6H, J=7Hz), 1.93 (m, 1H), 2.23 (s, 3H), 2.89 (d, 2H, J=7Hz), 4.44 (d, 1H, J=14Hz), 4.66 (d, 1H, J=14Hz) 6.58 (d, 2H, J=8Hz), 7.11 (t, 1H, J=8Hz), 7.28 (s, 2H)

M.p.: 140°-142° C. (decomp.)

EXAMPLE 46

Preparation of
2-[(2-isobutylamino-4-methyl)benzylthio]imidazole

The desired compound was prepared in the form of a pale yellow oil in the same manner as in Example 9.

$^1$H—NMR CDCl$_3$):δ
0.99 (d, 6H, J=7Hz), 1.94 (m, 1H), 2.27 (s, 3H), 2.94 (d, 2H, J=7Hz), 4.19 (s, 2H), 4.62 (br, 1H), 6.2–6.5 (m, 2H), 6.81 (d, 1H, J=7Hz), 7.03 (s, 2H)

EXAMPLE 47

Preparation of
2-[(2-isobutylamino-4-methyl)benzylsulfinyl]imidazole

The desired compound was prepared in the form of a white crystalline powder from 2-[(2-isobutylamino-4-methyl)benzylthio]imidazole obtained in Example 46 in the same manner as in Example 19.

IRν(KBr): cm$^{-1}$
3330, 2950, 2900, 1610, 1580, 1525, 1465, 1430, 1310, 1105, 1025, 755

$^1$H—NMR (CDCl$_3$/CD$_3$OD=1/1 vol/vol):δ
1.02 (d, 6H, J=7Hz), 1.93 (m, 1H), 2.26 (s, 3H), 2.88 (d, 2H, J=7Hz), 4.28 (d, 1H, J=14Hz), 4.51 (d, 1H, J=14Hz) 6.2–6.5 (m, 2H), 6.71 (d, 1H, J=7Hz), 7.23 (s, 2H)

M.p.: 141°–142° C. (decomp.)

EXAMPLE 48

Preparation of
2-[(2-chloro-6-isobutylamino)benzylthio]imidazole

The desired compound was prepared in the form of a white crystalline powder in the same manner as in Example 9.

$^1$H—NMR CDCl$_3$):δ
0.99 (d, 6H, J=6Hz), 1.95 (m, 1H), 2.89 (d, 2H, J=6Hz), 4.48 (s, 2H), 5.52 (br, 1H), 6.49 (dd, 1H, J=1Hz, 8Hz), 6.66 (dd, 1H, J=1Hz, 8Hz), 7.04 (t, 1H, J=8Hz), 7.04 (s, 2H)

EXAMPLE 49

Preparation of
2-[(2-chloro-6-isobutylamino)benzylsulfinyl]imidazole

The desired compound was prepared in the form of a white crystalline powder from 2-[(2-chloro-6-isobutylamino)benzylthio]imidazole obtained in Example 48 in the same manner as in Example 19.

IRν(KBr): cm$^{-1}$
3340, 2950, 2900, 1590, 1570, 1510, 1450, 1410, 1095, 1070, 1020, 770, 750

$^1$H—NMR (CDCl$_3$/CD$_3$OD=1/1 vol/vol):δ1.02 (d, 6H, J=7Hz), 1.94 (m, 1H), 2.89 (d, 2H, J=7Hz), 4.71 (s, 2H), 6.60 (dd, 1H, J=1Hz, 8Hz), 6.74 (dd, 1H, J=1Hz, 8Hz), 7.14 (t, 1H, J=8Hz), 7.28 (s, 2H)

M.p.: 163–164.5° C. (decomp.)

EXAMPLE 50

Preparation of
2-[(2-isobutylamino-3-methyl)benzylthio]imidazole

The desired compound was prepared in the form of a pale brown crystalline powder in the same manner as in Example 9.

$^1$H—NMR (CDCl$_3$):δ
1.02 (d, 6H, J=7Hz), 1.90 (m, 1H), 2.29 (s, SH), 2.80 (d, 2H, J=7Hz), 4.21 (s, 2H), 6.6–7.1 (m, 5H)

EXAMPLE 51

Preparation of
2-[(2-isobutylamino-3-methyl)benzylsulfinyl]imidazole

The desired compound was prepared in the form of a white crystalline powder from 2-[(2-isobutylamino-3-methyl)benzylthio]imidazole obtained in Example 50 in the same manner as in Example 19.

IRν(KBr): cm$^{-1}$
3350, 2950, 2000, 1460, 1430, 1415, 1230, 1140, 1090, 1025, 750

$^1$H—NMR (CDCl$_3$/CD$_3$OD=S/1 vol/vol):δ
1.04 (d, 6H, J=7Hz), 1.89 (m, 1H), 2.30 (s, 3H), 2.74 (d, 2H, J=7Hz), 4.39 (d, 1H, J=13Hz), 4.62 (d, 1H, J=13Hz) 6.5–7.3 (m, 3H), 7.21 (s, 2H)

M.p.: 144°–147° C. (decomp.)

EXAMPLE 52

Preparation of
2-[(2-isobutylamino-3-methoxy)benzylthio]imidazole

The desired compound was prepared in the form of a pale yellow crystalline powder in the same manner as in Example 9.

$^1$H—NMR (CDCl$_3$):δ
1.02 (d, 6H, J=7Hz), 1.89 (m, 1H), 2.85 (d, 2H, J=7Hz), 3.83 (s, 3H), 4.19 (s, 2H), 6.5–7.2 (m, 3H), 6.99 (s, 2H)

EXAMPLE 53
Preparation of
2-[(2-isobutylamino-3-methoxy)benzylsulfinyl]imidazole The desired compound was prepared in the form of a white crystalline powder from 2-[(2-isobutylamino-3-methoxy)benzylthio]imidazole obtained in Example 52 in the same manner as in Example 19.

IRν(KBr): cm$^{-1}$
3440, 2950, 2870, 2840, 1580, 1475, 1440, 1415. 1285, 1255. 1230, 1100, 1070, 1050, $^1$H—NMR (CDCl$_3$/CD$_3$OD=3/1 vol/vol):δ
0.99 (d, 6H, J=6Hz), 1.82 (m, 1H), 2.84 (d, 2H, J=7Hz), 3.84 (s, 3H), 4.39 (d, 1H, J=13Hz), 4.63 (d, 1H, J=13Hz) 6.3–6.9 (m, 3H), 7.21 (s, 2H)

M.p.: 109–112° C. (decomp.)

EXAMPLE 54

Preparation of
2-[(3-methyl-2-methylamino)benzylthio]imidazole

The desired compound was prepared in the form of a white crystalline product in the same manner as in Example 9.

$^1$H—NMR (CDCl$_3$):δ
2.30 (s, 3H), 2.80 (s, 3H), 4.24 (s, 2H), 6.5–7.2 (m, 5H)

EXAMPLE 55

Preparation of
2-[(3-methyl-2-methylamino)benzylsulfinyl]imidazole

The desired compound was prepared in the form of a white crystalline powder from 2-[(3-methyl-2-methylamino)benzylthio]imidazole obtained in Example 54 in the same manner as in Example 19.

IRν(KBr): cm$^{-1}$
3400, 3370, 2900, 1595, 1465, 1440, 1260, 1090, 1050, 1005, 960, 890, 780, 750, 500

$^1$H—NMR (CDCl$_3$/CD$_3$OD=2/1 vol/vol):δ
2.32 (s, 3H), 2.75 (s, 3H), 4.37 (d, 1H, J=13Hz), 4.60 (d, 1H, J=13Hz), 6.6–7.3 (m, 3H), 7.22 (s, 2H)

M.p.: 144°–146° C. (decomp.)

EXAMPLE 56

Preparation of 2-[(2-propylamino)benzylsulfinyl]imidazole

The desired compound was prepared in the form of a pale brown crystalline powder in the same manner as in Examples 9 and 19.

IRν(KBr): cm
3380, 2900, 1600, 1580, 1515, 1465, 1310, 1090, 1000, 890, 740, 500

$^1$H—NMR (CDCl$_3$/CD$_3$OD=2/1 vol/vol):δ
1.03 (t, 3H, J=7Hz), 1.68 (m, 2H), 3.04 (t, 2H, J=7Hz), 4.28 and 4.52 (each d, 2H, J=14Hz), 6.4–7.3 (m, 4H), 7.23 (s, 2H)

M.p.: 123–126° C. (decomp.)

EXAMPLE 57

Preparation of 2-[(2-butylamino)benzylsulfinyl]imidazole

The desired compound was prepared in the form of a pale brown crystalline powder in the same manner as in Examples 9 and 19.

IRν(KBr): cm$^{-1}$
3370, 2950, 1600, 1580, 1520, 1465, 1450, 1310, 1100, 1040, 740, 500

$^1$H—NMR (CDCl$_3$/CD$_3$OD=2/1 vol/vol):δ
0.98 (t, 3H, J=6Hz), 1.2–1.9 (m, 4H), 3.07 (t, 2H, J=6Hz), 4.29 and 4.52 (each d, 2H, J=14Hz), 6.4–7.3 (m, 4H), 7.23 (s, 2H)

M.p.: 136–139° C. (decomp.)

EXAMPLE 58

Preparation of 2-[(2-isobutylamino)thio]-4,5,6,7-tetrahydro-1H-benzimidazole

The desired compound was prepared in the form of a crystalline product in the same manner as in Example 9.

IRν(KBr): cm$^{-1}$
3410, 2920. 2840, 1600, 1575, 1510, 1460, 1380, 1320, 1310, 1270, 1000, 740

$^1$H—NMR (CDCl$_3$):δ
0.98 (d, 6H, J=7Hz), 1.5–2.2 (m, 5H), 2.2–2.7 (m, 4H), 2.94 (d, 2H, J=7Hz), 4.16 (s, 2H), 4.68 (br, 1H), 6.4–7.3 (m, 4H)

EXAMPLE 59

Preparation of 2-[(2-isobutylamino)benzylsulfinyl]-4,5,6,7-tetrahydro-1H-benzimidazole The desired compound was prepared in the form of a crystalline powder from 2-[(2-isobutylamino)benzylthio]4,5,6,7-tetrahydro-1H-benzimidazole obtained in Example 58 in the same manner as in Example 19.

IRν(KBr): cm$^{-1}$
3370, 2950, 2920, 2850, 1600, 1580, 1520, 1410, 1320, 1030, 740

$^1$H—NMR (CDCl$_3$):δ
0.97 (d, 6H, J=7Hz), 1.5–2.1 (m, 5H), 2.2–2.9 (m, 4H), 2.83 (d, 2H, J=6Hz), 4.25 (d, 1H, J=14Hz), 4.49 (d, 1H, J=14Hz), 4.87 (m, 1H), 6.4–7.3 (m, 4H), 10.7 (br, 1H)

M.p.: 163°–165° C. (decomp.)

EXAMPLE 60

Preparation of 4-ethyl-5-methyl-2-[(2-methylamino)benzylthio]imidazole

The desired compound was prepared in the form of a crystalline product in the same manner as in Example 9.

$^1$H—NMR CDCl$_3$):δ
1.14 (t, 3H, J=7Hz), 2.12 (s, 3H), 2.49 (q, 2H, J=7Hz), 2.81 (s, 2H), 4.09 (s, 2H), 6.4–7.3 (m, 4H)

EXAMPLE 61

Preparation of 4-ethyl-5-methyl-2-[(2-methylamino)benzylsulfinyl]imidazole

The desired compound was prepared in the form of a crystalline powder from 4-ethyl-5-methyl-2-[(2-methylamino)benzylthio]imidazole obtained in Example 60 in the same manner as in Example 10.

IRν(KBr): cm$^{-1}$
3200, 1005, 1580, 1520, 1315, 1045, 1030, 740

$^1$H—NMR (CDCl$_3$):δ
1.12 (m, 3H), 2.14 (s, 3H), 2.50 (q, 2H, J=8Hz), 2.69 (s, 3H), 4.24 (d, 1H, J=14Hz), 4.44 (d, 1H, J=14Hz), 4.9 (br, 1H), 6.4–7.4 (m, 4H), 11.3 (br, 1H)

M.p.: 120° C. (decomp.)

EXAMPLE 62

Preparation Example (Tablets)

Each tablet (220 mg) contained the following components:

| Effective component | 50 mg |
|---|---|
| Lactose | 103 |
| Starch | 50 |
| Magnesium stearate | 2 |
| Hydroxypropylcellulose | 15 |

EXAMPLE 63

Preparation Example (Capsules)

Each hard gelatin capsule (350 mg) contained the following components:

| Effective component | 40 mg |
|---|---|
| Lactose | 200 |
| Starch | 70 |
| Polyvinylpyrrolidone | 5 |
| Crystalline cellulose | 35 |

EXAMPLE 64

Preparation Example (Granules)

Each granule (1 g) contained the following components:

| Effective component | 200 mg |
|---|---|
| Lactose | 450 |
| Corn starch | 300 |
| Hydroxypropylcellulose | 50 |

We claim:
1. An imidazole derivative having the formula

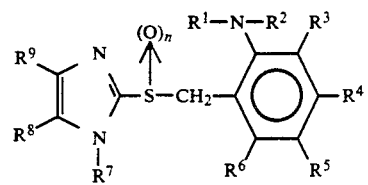

wherein
- each of $R^1$ and $R^2$ independently is hydrogen, an alkyl group having 1-8 carbon atoms, a cycloalkyl group having 5-8 carbon atoms, an aryl group, an aralkyl group having 1-4 carbon atoms in its alkyl chain, or a halogen atom-substituted alkyl group having 1-8 carbon atoms, or $R^1$ and $R^2$ are combined to form together with the nitrogen atom to which $R^1$ and $R^2$ are attached, a piperidine ring;
- each of $R^3$, $R^4$, $R^5$ and $R^6$ independently is hydrogen, a halogen atom, an alkoxy group having 1-6 carbon atoms, an araylkyloxy group having 1-4 carbon atoms in its alkyl chain, an alkyl group having 1-6 carbon atoms, an alkoxycarbonyl gruop having 2-7 carbon atoms, nitro, amino, an acyl having 1-6 carbon atoms, a fluorine substituted alkyl group having 1-6 carbon atoms, or a fluorine substituted alkoxy group having 1-6 carbon atoms;
- each of $R^8$ and $R^9$ independently is hydrogen, a halogen atom, an alkoxy group having 1-6 carbon atoms, an alkyl group having 1-5 carbon atoms, an alkoxycarbonyl group having 2-7 carbon atoms, nitro, amino, an acyl having 1-6 carbon atoms, a fluorine substituted alkyl group having 1-6 carbon atoms, or a fluorine substituted alkoxy group having 1-6 carbon atoms, provided that where $R^1$ and $R^2$ are combined to form a piperidine ring, $R^8$ and $R^9$ may be combined to form, together with two carbon atoms of the imidazole ring to which $R^8$ and $R^9$ is attached, a 5-8 membered alicyclic ring;
- $R^7$ is, where $R^8$ and $R^9$ are not combined, hydrogen and, where $R^8$ and $R^9$ are combined to form the alicyclic ring, hydrogen, an alkyl group having 1-6 carbon atoms which may have at least one substituent selected from the group consisting of an aryl group, hydroxyl, an alkoxy group having 1-6 carbon atoms, and a halogen atom, an aryl gruop which may have at least one substituent selected from the group consisting of an alkyl group having 1-6 carbon atoms, an alkoxy group having 1-6 carbon atoms, and a halogen atom, an arylcarbonyl group which may have at least one substituent selected from the group consisting of an alkyl group having 1-6 carbon atoms, an alkoxy group having 1-6 carbon atoms, and a halogen atom; and
- n is 0 or 1.

2. The imidazole derivative as claimed in claim 1 wherein n is 1.

3. The imidazole derivative as claimed in claim 1 wherein each of $R^1$ and $R^2$ independently is hydrogen, methyl ethyl, propyl, isopropyl, butyl, isobutyl, neopentyl hexyl, trifluoroethyl, cyclopentyl, cyclohexyl, phenyl, benzyl, benzyl substituted with one or more methyl and methoxy, phenylethyl, or phenylethyl substituted with chlorine.

4. The imidazole derivative as claimed in claim 1 wherein each of $R^3$, $R^4$, $R^5$ and $R^6$ may be same or different and is hydrogen, chlorine, fluorine, methoxy, ethoxy, benzyloxy, methyl, isobutyl, nitro, amino, trifluoromethoxy, acetyl, or methoxycarbonyl.

5. The imidazole derivative of claim 1 wherein each of $R^8$ and $R^9$ may be the same or different and is hydrogen, chlorine, methyl, ethyl, propyl, butyl, ethoxycarbonyl, trifluoromethyl, trifluoroethyl, phenyl, or nitro.

6. The imidazole derivative as claimed in claim 1 wherein $R^7$ is hydrogen.

7. The imidazole derivative as claimed in claim 1 wherein each of $R^3$, $R^5$, and $R^6$ may be the same or different and is hydrogen, a halogen atom, an alkoxy group having 1-6 carbon atoms, or an alkyl group having 1-6 carbon atoms, and $R^7$ is hydrogen.

8. The imidazole derivative of claim 1 wherein each of $R^1$, $R^2$, $R^3$, $R^5$, $R^5$, $R^6$, $R^8$ and $R^9$ may be the same or different and is hydrogen, methyl, ethyl, propyl, n-butyl, isobutyl, pentyl, or hexyl, and $R^7$ is hydrogen.

9. The imidazole derivative of claim 1 wherein $R^1$ is iso-butyl, each of $R^2$, $R^3$, $R^4$, $R^5$, $R^6$, $R^7$, $R^8$, And $R^9$ is hydrogen, an n is 1.

10. A composition containing an anti-ulcer effective amount of the compound of claim 1 and a pharmaceutically acceptable carrier.

11. A method for treating ulcers in a patient comprising administering to the patient anti-ulcer effective amount of the derivative of claim 1.

12. A method for treating ulcers in a patient comprising administering to the patient anti-ulcer effective amount of the composition of claim 7.

* * * * *